US011851390B2

(12) United States Patent
Pelckmans et al.

(10) Patent No.: US 11,851,390 B2
(45) Date of Patent: Dec. 26, 2023

(54) REACTION OF GLYCOLADEHYDE

(71) Applicant: Taminco BV, Ghent (BE)

(72) Inventors: Michiel Jules Y Pelckmans, Mol (BE); William Hendrick Faveere, Ghent (BE); Bert Sels, Westerlo (BE)

(73) Assignee: Taminco BVBA

( * ) Notice: Subject to any disclaimer, the term of this patent is extended or adjusted under 35 U.S.C. 154(b) by 223 days.

(21) Appl. No.: 17/044,471

(22) PCT Filed: Apr. 4, 2019

(86) PCT No.: PCT/EP2019/058557
§ 371 (c)(1),
(2) Date: Oct. 1, 2020

(87) PCT Pub. No.: WO2019/193117
PCT Pub. Date: Oct. 10, 2019

(65) Prior Publication Data
US 2021/0139410 A1    May 13, 2021

Related U.S. Application Data

(60) Provisional application No. 62/652,751, filed on Apr. 4, 2018.

(30) Foreign Application Priority Data

Apr. 2, 2019   (GB) ..................... 1904612

(51) Int. Cl.
C07C 213/08    (2006.01)
B01J 21/18     (2006.01)
B01J 23/44     (2006.01)
B01J 23/46     (2006.01)
C07C 209/26    (2006.01)

(52) U.S. Cl.
CPC ............ *C07C 213/08* (2013.01); *B01J 21/18* (2013.01); *B01J 23/44* (2013.01); *B01J 23/462* (2013.01); *C07C 209/26* (2013.01)

(58) Field of Classification Search
None
See application file for complete search history.

(56) References Cited

U.S. PATENT DOCUMENTS

| 2,941,005 | A  | 6/1960  | Maham |
| 6,147,261 | A  | 11/2000 | Knifton et al. |
| 6,534,441 | B1 | 3/2003  | Bartley et al. |
| 7,094,932 | B2 | 8/2006  | Majerski et al. |
| 7,405,327 | B2 | 7/2008  | Haese et al. |
| 7,420,093 | B2 | 9/2008  | Puckette et al. |
| 7,449,607 | B2 | 11/2008 | Almeida Lenero et al. |
| 7,511,178 | B2 | 3/2009  | Almeida Lenero et al. |
| 7,750,189 | B2 | 7/2010  | Kubanek et al. |
| 8,324,430 | B2 | 12/2012 | Kubanek et al. |
| 8,742,174 | B2 | 6/2014  | Magerlein et al. |
| 8,772,548 | B2 | 7/2014  | Magerlein et al. |

FOREIGN PATENT DOCUMENTS

| BG | 2279950 A | 1/1995 |
| CN | 107011194 A | 8/2017 |
| DE | 3609978 A1 | 10/1987 |
| DE | 4400591 A1 | 7/1995 |
| EP | 0394986 A2 | 10/1990 |
| EP | 1697291 A1 | 9/2006 |
| EP | 2542206 A1 | 1/2013 |
| EP | 3290401 A1 | 3/2018 |
| JP | 3246248 B2 | 1/2002 |
| JP | 3279342 B2 | 4/2002 |
| WO | WO 2009/027249 A2 | 3/2009 |
| WO | WO 2014/131764 A1 | 9/2014 |

OTHER PUBLICATIONS

Haynes et al. (CRC Handbook of Chemistry and Physics, 94 Ed., 2014, Section 15: Practical Laboratory Data, Laboratory Solvents and Other Liquid Reagents), (Year: 2014).*
Reichardt (Solvents and Solvent Effects in Organic Chemistry, 3rd Ed., 2003, Wiley-VCH) (Year: 2003).*
Davis (Acid-Base Behavior in Aprotic Organic Solvents, 1968, National Bureau of Standards Monograph 105) (Year: 1968).*
Atienza (Amination: An Overview, 2008) (Year: 2008).*
Machine English translation of Wang et al. (CN 107011194, pub date 2017) (Year: 2017).*
Human English translation of Wang et al. (CN 107011194, pub date 2017) (Year: 2017).*
Pelckmans, M., et al.; "Bio-based amines through sustainable heterogeneous catalysis"; Green Chem., 2017, 19. pp. 5303-5331.
Froidevaux, Vincent, et al.; "Biobased Amines: From Synthesis to Polymers; Present and Future"; Chemical Reviews 2016, 116, pp. 14181-14224.
Wang, Hongliang, et al.; "Effects of Lignin Structure on Hydrodeoxygenation Reactivity of Pine Wood Lignin to Valuable Chemicals"; ACS Sustainable Chemistry & Engineering 2017, 5, pp. 1824-1830.
Pelckmans, Michael, et al.; "Low-Temperature Reductive Aminolysis of Carbohydrates to Diamines and Aminoalcohols by Heterogeneous Catalysis"; Angewandte Chemie 2017, 56, pp. 14540-14544.
Kroh, Lothar W .; "Caramelisation in food and beverages"; Food Chemistry 51 (1994), pp. 373-379.

(Continued)

*Primary Examiner* — Sudhakar Katakam
*Assistant Examiner* — Jennifer C Sawyer
(74) *Attorney, Agent, or Firm* — Kenrick L. Vidale

(57) ABSTRACT

A two-step one-pot process for reacting glycolaldehyde with an aminating agent in the presence of a reactive organic fluid for instance a reactive solvent is provided. The first step comprises of contacting glycolaldehyde with an aminating agent in the presence of a reactive fluid for instance a reactive solvent under inert atmosphere to produce unsaturated intermediates, and reacting the reaction mixture obtained in step 1 with hydrogen in the presence of a supported hydrogenation catalyst in a second step.

17 Claims, No Drawings

(56) References Cited

OTHER PUBLICATIONS

Poissonnier, Jeroen, et al.; "Kinetics of homogeneous and heterogeneous reactions in the reductive aminolysis of glucose with dimethylamine"; Applied Catalysis B: Environmental, 227, (2018), pp. 161-169.

Althoff, Eric A., et al.; "Robust design and optimization of retroaldol enzymes"; Protein Science 2012, vol. 21, pp. 717-726.

Giger, Lars, et al.; "Evolution of a designed retro-aldolase leads to complete active site remodeling"; Nat. Chem. Biol. (2013), 9 (8): pp. 494-498.

Runeberg, Johan et al.; "Copper Catalyzed Amination of Ethylene Glycol"; Applied Catalysis, 17, (1985), pp. 309-319.

Patil, Mahendra P., et al.; "Insights on Co-Catalyst-Promoted Enamine Formation between Dimethylamine and Propanal through Ab Initio and Density Functional Theory Study"; J. Org. Chem. (2007), 72, pp. 8202-8215.

Yaylayan, Varoujin, et al.; "Investigation of the mechanism of dissociation of glycolaldehyde dimer (2,5-dihydroxy-1,4-dioxane) by FTIR spectroscopy"; Carbohydrate Research (1998), 309, pp. 31-38.

Kluson, Petr, et al.; "Preparation and properties of ruthenium supported catalysts"; Catalysis Letters 23, (1994), pp. 299-312.

Jiang, Li, et al.; "De Novo Computational Design of Retro-Aldol Enzymes"; Science, vol. 319, (2008), pp. 1387-1391.

Reichardt, Christian; "Solvents and Solvent Effects in Organic Chemistry"; 3$^{rd}$ edition, (2003), pp. 82-84.

Safariamin, M., et al.; "Novel direct amination of glycerol over heteropolyacid-based catalysts"; Catal. Sci. Technology, 2016, 6, pp. 2129-2135.

Kusserow, Burkhard et al.; Hydrogenation of Glucose to Sorbitol over Nickel and Ruthenium Catalysts; Adv. Synth. Catal. (2003), 345, pp. 289-299.

De Bruijn, J.M., "Reactions of Monosaccharides in Aqueous Alkaline Solutions"; Sugar Technology Reviews, 13 (1986), pp. 21-52.

Notification of Transmittal of the International Search Report and the Written Opinion of the International Searching Authority with Date of Filing Apr. 4, 2019 for International Application No. PCT/EP2019/058557.

\* cited by examiner

REACTION OF GLYCOLADEHYDE

CROSS-REFERENCE TO RELATED APPLICATION(S)

This application is a national stage filing under 35 USC § 371 of International Application Number PCT/EP2019/058557, filed on, Apr. 4, 2019 which claims the benefit of the filing date to U.S. Provisional Application No. 62/652,751, filed on Apr. 4, 2018, and GB 1904612.7 filed on Apr. 2, 2019, the entire disclosures of which are incorporated by reference herein.

BACKGROUND AND SUMMARY

Background of the Invention

A. Field of the Invention

The present invention concerns a reaction of glycolaldehyde with an aminating agent in a two-step procedure and in the presence of a reactive fluid for instance a reactive organic liquid.

B. Description of the Related Art

Industrially, (N-substituted) alkanolamines are produced almost exclusively by reacting ethylene oxide with ammonia or other primary, secondary or tertiary amines. Diamines are commonly produced by reacting an amine of the former with 1,2-dichloroethane, ethylene glycol or monoethanolamine. Also consecutive reaction can take place yielding in higher alkanolamines, e.g. diethanolamine or triethanolamine in case of ammonia, but also heterocyclic compounds like piperazine as a consequence of an intramolecular reaction. These (N-substituted) alkanolamines and diamines typically find their applications in the production of emulsifiers, detergent raw materials, textile chemicals, curing agents, gas purification, agrochemicals etc.

The educts used for manufacturing of (N-substituted) alkanolamines and diamines such as ethylene oxide, ethylene glycol, 1,2-dichloroethane or monoethanolamine, however, are typically obtained through functionalization of a C2 petrochemical feedstock, in particular ethylene. In view of the fact that petrochemical raw materials will become more and more difficult to obtain in the future, it is desirable to discover new, raw materials preferably from renewable sources for manufacturing (N-substituted) alkanolamines and diamines.

The reaction of hydroxyl-substituted aldehydes with aminating agents is already known from the prior art. U.S. Pat. Nos. 7,750,189B2, 7,405,327B2 and 8,324,430B2 relates to the one-step amination of alcohols, aldehydes and ketones with hydrogen and a nitrogen compound in the presence of a Zr-, Ni- and/or Cu-containing catalyst. U.S. Pat. No. 6,147,261A relates to the production of diaminoalkanes by contacting a hydroxyalkanal with an excess of ammonia and hydrogen in a one-step process. Although the abovementioned references generically encompass the reaction of aldehydes, including hydroxyl-substituted aldehydes, the two-step one-pot reaction of glycolaldehyde in the presence of a reactive fluid for instance a reactive solvent is not disclosed.

U.S. Pat. No. 6,534,441B1 described a process for reductive amination of lower aliphatic alkane derivatives using a nickel/rhenium catalyst. German patent application DE-A1-4400591 describes a process for preparing amino alcohols by reaction of hydroxyl carbonyl compounds with hydrogen and an aminating agent in a one-step process. The reaction can be performed in presence or absence of an inert solvent and with an activated ruthenium catalyst that has been activated by reducing a catalytic precursor with hydrogen prior to use. Although both patents mention glycolaldehyde as a possible feedstock, the specific reaction demonstrated by examples has not been described.

U.S. Pat. No. 6,147,261A described a process for diaminoalkane synthesis via selective amination of hydroxyaldehydes. Although the hydroxyaldehydes are defined as hydrocarbons having from two to six carbons and characterized by dual functionalities, the main substrate used herein is 3-hydroxypropanal. Preferred solvents may include water and hydrocarbons, with the exception of primary and secondary alcohols. A two-step process is mentioned, wherein the corresponding alcohol is formed in the first process stage in the presence of hydrogen, and is converted to propylenediamine in a subsequent second stage. Patent EP0394986A1 describes the amination of carbonyls with Raney Nickel and Raney Cobalt catalysts. Herein, a two stage process is described where the ketonitrile is first contacted with the aminating agent to form the corresponding imine or enamine, followed by a subsequent hydrogenation to the corresponding amine in a second step. Glycolaldehyde is not explicitly disclosed as a substrate. The process is conducted in the presence of an inert solvent towards amination, but mentions methanol to have a role in minimizing the catalyst deactivation at process conditions. German patent DE36009978A1 describes a process for preparing hydroxy amines from hydroxyl carbonyl compounds. The carbonyl compound is first reacted with the aminating agent to obtained the corresponding imine in a first step, followed by subsequent hydrogenation to the corresponding amine in a second step. U.S. Pat. No. 2,941,005 describes a two-step procedure for preparing 1,2-diamino-1-alkene compounds in the application of rocket fuels, by reacting dimethylamine with an alpha-halo-aldehyde such as chloroacetaldehyde in a first step, and the obtained enamine product could be optionally hydrogenated in a second step. European patent EP3290401A1 describes a two-step one-pot method in a fed-batch reactor for the creation of N-substituted acyclic ethylene diamines (64C %) in the solvent-free reductive aminolysis of carbohydrates. A similar route of the preparation of N-substituted acyclic ethylene diamines as ligands for homogeneous catalysts has been described by GB2279950, providing a one-step method for self-condensing an appropriate aminoalcohol in the presence of hydrogen, solvent and copper catalyst. Although these patents mention the role of a two-stage process for a better formation of intermediates in the creation of amines, the two-step one-pot process has not been mentioned for the amination of glycolaldehyde as such.

U.S. Pat. No. 8,772,548B2 described the one-step reaction of glycolaldehyde with an aminating agent in the presence of hydrogen, a catalyst comprising of Ni, Co and/or Cu and an inert solvent. Preferential solvents are water and THF, and preference is given to ammonia as an aminating agent. In a reaction at 100° C. and 100 bar of hydrogen pressure for 8 hours, glycolaldehyde was contacted with ammonia at a molar ratio ($NH_3$:GA) of 35. A conversion of 100% is obtained, with maximum selectivity of 82% for monoethanolamine (MOEA) and 17% of ethylenediamine (EDA) and no higher alkanolamines such as diethanolamine (DEOA) and triethanolamine (TEOA) are obtained. It is said that a solvent used must be inert under the reaction conditions and has to have sufficient solubility for the reactants and reaction product. The following patent, U.S. Pat. No. 8,742,174B2, contacts the MEOA derived from glycolaldehyde with a new stream of glycolaldehyde to obtain higher alkanolamines. With MEOA (molar ratio 5) as an aminating agent, up to 56% (sel.) of DEOA is obtained at 70% conversion. Starting with DEOA (molar ratio 2) as an aminating agent yields up to 88% selectivity of TEOA at 70% conversion. Although these patents mention other amines (methylamine, dimethylamine, . . . ) as possible aminating agents, the specific reactions demonstrated by examples has not been described. Furthermore, a one-pot process to obtain higher alkanolamines straight from glycolaldehyde has not been mentioned.

Previous examples have repeatedly mentioned the use of an inert solvent towards amination, with the intention to avoid polymerization and/or ease of separation. U.S. Pat. No. 6,147,261A teaches that hydroxyl-substituted aldehydes such as 3-hydroxypropanal are very reactive and tends to polymerization, and is therefore preferentially conducted in a solvent. Glycolaldehyde has an ever greater tendency to form the dimer, 2,5-dihydroxy-1,4-dioxane, a six-membered ring compound formed preferentially owing to its thermodynamic stability. Glycolaldehyde in the solid form solely exists in dimeric form (V. Yaylayan, S. Harty-Majors, A. Ismail, Carbohydrate Research, 309 (1998), 31-38). In aqueous solution, glycolaldehyde exists mainly in the form of the hydrate, and only 4% of glycolaldehyde is present in monomeric form. In addition, glycolaldehyde as a CH-acidic compound, has a high tendency to polymerize in an aldol condensation or undergo Maillard reactions in the presence of amines, which forms highly colored products and reduces the yield of target product.

Yet there remains a need for improved methods and means to glycolaldehyde amination which comprise an increased amination of glycolaldehyde with high conversion rates in a one-pot process, and a high tuneable selectivity towards preferred products such as N-substituted alkanolamines, diamines and higher alkanolamines. These and other problems are solved as described hereinafter in the summary, detailed embodiments, examples, drawings and claims.

SUMMARY OF THE INVENTION

It was an object of the present invention to develop a one-pot process for the amination of glycolaldehyde with high conversion rates, and a high tuneable selectivity towards preferred products such as N-substituted alkanolamines, diamines and higher alkanolamines. In addition, the reaction products should be obtained in a high purity.

The present invention solves the problems of the related art by a two-step one-pot process for reacting glycolaldehyde with an aminating agent in the presence of hydrogen, catalyst and a reactive fluid for instance a reactive solvent. In one aspect of the invention, the presence of a reactive fluid for instance a reactive solvent enables to attain higher product selectivity. Another aspect of the invention is that the benefits of a reactive fluid for instance a reactive solvent can be exploited to a maximum by means of a two-step one-pot process with the aim of maximizing the conversion towards key imine and enamine intermediates. In still another aspect of the invention, selectivity between higher alkanolamines and/or diamine products can be chosen by applying an appropriate amine-to-substrate ratio in combination with this two-step one-pot process in the presence of a reactive fluid for instance a reactive solvent to obtain product yields beyond the state.

According to the present invention there is provided a process for preparing alkanolamines and diamines, characterized by a two-step procedure wherein step 1 comprises under inert atmosphere and in a reactive organic fluid reacting of glycolaldehyde with an aminating agent, whereof at least part of molecules of the organic fluid contain a labile H+ or have an acidic, eventually weak acidic hydrogen, to give unsaturated intermediates and step 2 comprises hydrogenating the reaction mixture obtained in the first step under a hydrogen atmosphere whilst in contact with a supported hydrogenation catalyst and still in the reactive organic fluid or there is provide a process for preparing alkanolamines and diamines, the process characterized by a two-step procedure wherein step 1 comprises reacting glycolaldehyde with an aminating agent in a reactive organic fluid and under an inert atmosphere to give unsaturated intermediates, and step 2 comprises hydrogenating the reaction mixture obtained in the first step under a hydrogen atmosphere whilst in contact with a supported hydrogenation catalyst. This embodiment of the invention advantageously comprises that the organic fluid comprises molecules that have an hydrogen atom bound to an oxygen (as in a hydroxyl group) or bound to an nitrogen (as in an amine group) so that the organic fluid readily participates in the formation of unsaturated intermediates by donating protons (H+). This embodiment of the invention also advantageously comprises that the inert atmosphere is nitrogen. In another aspect, the present invention provides that the glycolaldehyde and aminating agent are solutes in the organic fluid of the first step or that the reaction mixture obtained in the first step are solutes in the organic fluid. In an advantageous embodiment, the device according to the present invention further comprises that reaction is conducted in a two-step one-pot procedure.

In another aspect, the process of present invention provides that the first step comprises reacting the glycolaldehyde with an aminating agent of the groups consisting of ammonia (NH3), at least one primary amine (NH2R) and at least one secondary amine (NHR'R") and in contact with, solved in or in the presence of the organic fluid to give unsaturated intermediates. In yet another aspect, the process of present invention provides that the aminating agent is ammonia, monomethylamine or dimethylamine.

In yet another aspect, the process of present invention provides that the solid catalyst is a supported hydrogenation catalyst.

In yet another aspect, the process of present invention provides that the solid catalysts comprises Pd or Ru, as catalytically active components.

In yet another aspect, the process of present invention provides that the solid catalysts comprises, silica, silica-alumina, alumina or carbon, as support In yet another aspect, the process of present invention provides that the solid catalyst is Ru/C or comprises Ru/C or is Pd/C or comprising Pd/C.

In yet another aspect, the process of present invention provides that the amine-to-substrate molar ratio is between 1/3 to 40/1 at start in the first step.

In yet another aspect, the process of present invention provides that the amine-to-substrate molar ratio is stoichiometric according to the obtained final product.

In yet another aspect, the process of present invention provides that the reactions are performed at a reaction temperature of 15 to 250° C. and at a reaction pressure or a pressure during the reaction of 10 to 150 bar.

In yet another aspect, the process of present invention provides that the reaction products obtained in a one-pot process starting from ammonia (NH3) are monoethanolamine, diethanolamine, triethanolamine or ethylene diamine.

In yet another aspect, the process of present invention provides that the reaction products obtained in a one-pot process starting from monomethylamine (MMA) are N-methylaminoethanol, N-methyldiethanolamine or N,N'-dimethylethylenediamine.

In yet another aspect, the process of present invention provides that the reaction products obtained in a one-pot process starting from dimethylamine (DMA) are N,N-dimethylaminoethanol or N,N,N',N'-tetramethylethylenediamine.

In yet another aspect, the process of present invention provides that the alkanolamines are obtained in a one-pot process with methanol as reactive fluid.

In yet another aspect, the process of present invention provides that the alkanolamines are obtained in a one-pot process with methanol as reactive fluid and stoichiometric amine-to-substrate molar ratio according to the obtained final alkanolamine product.

In yet another aspect, the process of present invention provides that the alkanolamines are obtained in a two-step one-pot process with methanol as reactive fluid.

In yet another aspect, the process of present invention provides that the alkanolamines are obtained in a two-step one-pot process with methanol as reactive fluid and stoichiometric amine-to-substrate molar ratio according to the obtained final alkanolamine product.

In yet another aspect, the process of present invention provides that the diamines are obtained in a two-step one-pot process with ethylene glycol as reactive fluid.

In yet another aspect, the process of present invention provides that the diamines are obtained in a two-step one-pot process with ethylene glycol as reactive fluid and stoichiometric amine-to-substrate molar ratio according to the obtained final diamine product.

In yet another aspect, the process of present invention provides that the organic fluid is a polar protic organic fluid.

In yet another aspect, the process of present invention provides that the organic fluid is protic and polar and has an high dielectric constant (dielectric constant of greater than or equal to 15) and high polarity (polarity index (P) above 5 and/or relative polarity above 0.400).

In yet another aspect, the process of present invention provides that the organic fluid polar protic organic fluid and has a dielectric constant of a value between 15 to 50 or of a value between 25 to 45 or of a value between 20 or 90.

In yet another aspect, the process of present invention provides that the organic fluid polar protic organic fluid and has a dipole moment that is larger than 1.4 Debye or that is larger than 1.5 Debye.

In yet another aspect, the process of present invention provides that the organic fluid polar protic organic fluid and has a polarity index is of a value between 3 to 9 or a polarity index is of a value between 1.8 to 2.

In yet another aspect, the process of present invention provides that the organic fluid is composed of or comprises molecules with 1 to 4 C atoms.

In yet another aspect, the process of present invention provides that the organic fluid is an alcohol of the group consisting of methanol, ethanol and ethylene glycol.

In yet another aspect, the process of present invention provides that the process reactions are in the absence of water.

In yet another aspect, the process of present invention provides that the organic fluid is reactive under hydrogenation reaction conditions.

In yet another aspect, the process of present invention provides that the organic fluid is catalytic under hydrogenation reaction conditions.

In yet another aspect, the process of present invention provides that the organic fluid disperses the reactants and reaction products.

In yet another aspect, the process of present invention provides that the organic fluid solves the reactant and reaction product solutes.

DETAILED DESCRIPTION

Detailed Description of Embodiments of the Invention

Detailed Description of the Invention

The term "solvent" is used conventionally to mean chemical fluid into which a solute, is dissolved or dispersed.

An "inert solvent" is conventionally used for a solvent that does not react with anything in solution or a solvent that is inert under specific reaction conditions. For instance according to the method described in EP2542206 alkoxylation can be carried out by the use of a solvent which is inert under the alkoxylation.

The term "fluid" is conventionally used for substance that continually deforms (flows) under an applied shear stress, or external force. Fluids are a phase of matter and include liquids, gases and plasmas. They are substances with zero shear modulus, or, in simpler terms, substances which cannot resist any shear force applied to them. This term "fluid" includes both the liquid and gas phases The term "reactive solvent" is used for a solvent that does not react with anything in solution under the specific reaction conditions, but participates in the formation of unsaturated intermediates, thus having a role as co-catalyst in the formation of imines and enamines. Preference is given to polar protic organic fluids such as alcohols, having a labile H+ or (weakly) acidic hydrogen atom, which can be donated to help the formation of unsaturated intermediates.

The term "polar" is used conventionally to mean hydrophilic or lipophobic; while the term non-polar is used conventionally to mean hydrophobic or lipophilic. For instance polar substances have large dipole moments (aka "partial charges"); they contain bonds between atoms with very different electronegativities, such as oxygen and hydrogen. Non polar substances contain bonds between atoms with similar electronegativities, such as carbon and hydrogen (think hydrocarbons, such as gasoline). Bonds between atoms with similar electronegativities will lack partial charges; it's this absence of charge which makes these molecules "non-polar".

There are two common ways of measuring this polarity. One is through measuring a constant called "dielectric constant" or permittivity. The greater the dielectric constant, the greater the polarity (water=high, gasoline=low).

The term "polar molecule" for the purpose of the specification and claims, can be understood as a molecule that is readily miscible with glycerol, can solubilize salt to only low levels if at all, and has a lower boiling point than glycerol. It also concerns molecules that have the polar characteristics as described above. Examples of such polar molecules are alcohols, including but not limited to, isopropanol or isopropyl alcohol (IPA), 1-propanol, 1-butanol, 2-butanol, tert-butanol, ethanol, and methanol.

The term "polar organic fluid" for the purpose of the specification and claims, can be understood as an organic fluid that is readily miscible with glycerol, can solubilize salt to only low levels if at all, and has a lower boiling point than glycerol. It also concerns organic fluids that have the polar characteristics as described above. Examples of such polar organic fluids are fluid forms alcohols, including but not limited to, isopropanol or isopropyl alcohol (IPA), 1-propanol, 1-butanol, 2-butanol, tert-butanol, ethanol, and methanol. Another example of a polar organic fluid is phenol.

The term "protic" refers to the presence of a labile proton like a hydroxyl proton or carboxylic acid proton. In chemistry, a protic solvent is a solvent that has a hydrogen atom bound to an oxygen (as in a hydroxyl group), a nitrogen (as in an amine group) or a fluorine (as in hydrogen fluoride). In general terms, any solvent that contains a labile H+ is called a protic solvent. The molecules of such solvents readily donate protons (H+) to reagents. Conversely, aprotic solvents cannot donate protons. "Aprotic" means the absence of labile protons. And protic molecule means such molecule with the presence of a labile proton like a hydroxyl proton or carboxylic acid proton or a molecule that has a hydrogen atom bonded to an electronegative atom, yielding highly polarized bonds in which the hydrogen has protonlike character and can have hydrogen bonding characteristics. "The term "protic organic molecule" is thus an organic molecule with these protic characteristics and described for instance in C. Reichardt, "Molecules and Molecule Effects in Organic Chemistry", 3rd edition, p. 82-84, 2003, Wiley-VCH, Weinheim, protic molecules contain hydrogen atoms bonded to electronegative elements. Typical examples of these are alcohols, amines (amines are to be understood as meaning aliphatic and cycloaliphatic amines), acid amides and carboxylic acids. They can be, in particular, lower alcohols, such as, in particular, methanol, ethanol, 1-propanol, 2-propanol, 1-butanol, 2-butanol, 2-methyl-1-propanol and/or 2-methyl-2-propanol, preferably methanol, ethanol, propanol and/or butanol. The particularly advantageous protic molecules furthermore include glycols, amines, acid amides and carboxylic acids, preferably glycols, such as monoethylene glycol, diethylene glycol, mono-1,2-propylene glycol, di-1,2-propylene glycol, 1,2-butylene glycol, 2,3-butylene glycol and/or glycerol, and amines, such as methylamine, ethylamine, n-propylamine, i-propylamine, n-butylamine, dimethylamine, diethylamine, di-n-propylamine, di-n-butylamine, pyrrolidine, piperidine, piperazine, N-methylpiperazine, N-ethylpiperazine, morpholine, ethylenediamine, 1,2-propylenediamine, 1,3-propylenediamine, di-(2-cyanoethyl)amine, di-(2-amino-ethyl)amine, tri-(2-aminoethyl)amine, ethanolamine, diethanolamine, triethanolamine, propanolamine, dipropanolamine and/or tripropanolamine. These protic organic molecule can be in a gas or liquid phase.

"Aprotic" means the absence of labile protons and "aprotic organic molecule" refers to organic molecules that cannot donate protons. For instance a molecule without hydroxyl, such as tetrahydrofuran, ether, dichloromethane, acetone, acetonitrile, DMF, and the mixtures thereof, preferably tetrahydrofuran". Examples of aprotic organic molecules include acetone, acetonitrile, dimethylformamide, toluene (C6H5-CH3), xylene (ortho-xylene, meta-xylene or para-xylene), chlorobenzene (MCB), heptane, tetrahydrofuran (THF), 2-methyltetrahydrofuran (CH3-THF), methyl-tert-butyl-ether (MTBE), 1,4-dioxane, ethyl acetate (EtOAc), butyl acetate, acetone or acetonitrile.

Protic organic solvents have O—H or N—H bonds so that protic substances can participate in hydrogen bonding (a powerful intermolecular force) and additionally these O—H or N—H bonds can serve as a source of protons (H+). It also concerns organic solvents that have the protic characteristics as described above.

Aprotic organic solvents may have hydrogens on them somewhere, but they lack O—H or N—H bonds, and therefore cannot donate hydrogen bonds. Examples of polar aprotic fluids unsuitable for present invention are water-miscible open-chain ethers, for example triethylene glycol dimethyl ether, poly (ethylene glycol) di-methyl ether, water-miscible cyclic ether, such as dioxane or THF, as well as DMSO, NMP and DMF.

The term "protic organic fluid" refers to a type of organic fluid with hydroxyl (i.e., —OH), such an alcohol, such as methanol, ethanol and generally includes fluids that have a hydrogen atom bound to an oxygen atom (as in a hydroxyl group) or a nitrogen atom (as in an amine group), so that they can principally donate protons (H+) to reagents. It also concerns organic fluids that have the protic characteristics as described above. Preferred protic organic fluids include C1-C4-alkanols, C2-C4-alkandiols, ether alkanols, acetic acid, formic acid, and mixtures thereof. C1-C4-alkanols generally include methanol, ethanol, propanol, isopropanol, n-butanol, sec-butanol, and tert-butanol. Preferred C1-C4-alkanols include methanol (MeOH), ethanol (EtOH), n-propanol and isopropanol. Preferred are methanol and ethanol. Particularly preferred fluid is methanol. Preferred C2-C4-alkandiols include ethylene glycol or propylene glycol.

Examples of polar protic organic fluids are alcohols, in particular 1 to 4 C atoms—alcohol with, for example methanol, ethanol, n-propanol, iso-propanol, n-butanol, iso-butanol or tert-butanol, or also diols or polyalcohols, for example ethylene glycol, propylene glycol, glycerol, polyethylene glycols, for example PEG1000 PEG600 and, as well as alkoxy—alcohols, for example Methoxyethanol or Ethoxyethanol." Polar protic organic fluids also concerns organic fluids that have the polar and protic characteristics as described above.

The term "alkanolamines" within the context of the present application means molecules according to the following formula:

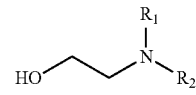

The term "diamines" within the context of the present application means molecules according to the following formula:

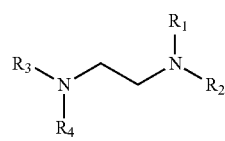

The term "unsaturated intermediates" within the context of the present application means molecules such as imines, enamines, amino aldehydes who can be tautomers of each other depending on the type of aminating agent used, according to the following formulas:

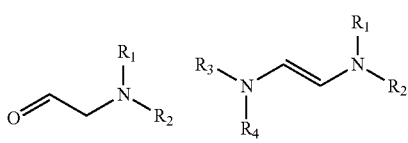

wherein the residues $R_1$, $R_2$, $R_3$ and $R_4$ can be identical or different from each other. In particular, the residues $R_1$, $R_2$, $R_3$ and $R_4$ are determined by the residues R, R', R" of the at least one primary amine NH2R, respectively the at least one secondary amine NHR'R" or the mixture of the at least one primary amine or the at least one secondary amine used as educts in the methods according to the invention. Consequently, the residues $R_1$, $R_2$, $R_3$ and $R_4$ are each independently selected from hydrogen, linear alkyl groups, branched alkyl groups, linear hydroxy alkyl groups, branched hydroxy alkyl groups, cyclic alkyl groups, which may be substituted and aromatic groups, which may be substituted. Further, the residues $R_1$, $R_2$, $R_3$ and $R_4$ can form together with the nitrogen atom to which the residues $R_1$, $R_2$, $R_3$ and $R_4$ are attached a heterocyclic alkyl group or a heterocyclic aromatic group, like piperidine, pyrrolidine, morpholine, piperazine or oxazolidine which may be substituted on the carbon ring.

The residues $R_1$, $R_2$, $R_3$ and $R_4$ can be each independently selected from hydrogen, methyl, ethyl, n-propyl, iso-propyl, n-butyl, s-butyl, t-butyl, iso-butyl, n-pentyl, sec-pentyl, isopentyl, n-hexyl, sec-hexyl, iso-hexyl, cyclohexyl, hydroxy ethyl, hydroxyl propyl, hydroxy-iso-propyl, 1,2-dihydroxy propyl, 1-hydroxy butyl, 2-hydroxy butyl, 3-hydroxy butyl, 4-hydroxy butyl, 1-hydroxy pentyl, 2-hydroxy pentyl, 3-hydroxy pentyl, 4-hydroxy pentyl, 5-hydroxyl pentyl, 1-hydroxy hexyl, 2-hydroxy hexyl, 3-hydroxy hexyl, 4-hydroxy hexyl, 5-hydroxy hexyl, 6-hydroxy-hexyl, toluyl, phenyl, 2-ethyl hexyl.

The term "primary amine" within the context of the present application means a molecule which is capable of acting as an aminating agent and having the formula NH2R, wherein the residue R is selected from linear or branched alkyl groups, linear or branched alkanol groups, cyclic alkyl groups which may be substituted and aromatic groups, which may be substituted.

In particular, residue R can be selected from methyl, ethyl, hydroxy ethyl, hydroxyl propyl, hydroxy-iso-propyl, 1,2-dihydroxy propyl, 1-hydroxy butyl, 2-hydroxy butyl, 3-hydroxy butyl, 4-hydroxy butyl, 1-hydroxy pentyl, 2-hydroxy pentyl, 3-hydroxy pentyl, 4-hydroxy pentyl, 5-hydroxy pentyl, 1-hydroxy hexyl, 2-hydroxy hexyl, 3-hydroxy hexyl, 4-hydroxy hexyl, 5-hydroxy hexyl, 6-hydroxy hexyl, toluyl or phenyl.

Examples of primary amines suitable to be used in the methods according to the invention can be selected from methylamine, ethylamine, 2-ethanolamine, n-propylamine, isopropylamine, 3-propanolamine, isopropanolamine, 3-aminopropane-1,2-diol, n-butylamine, s-butylamine, isobutylamine, 2-butanolamine, 3-butanolamine, 4-butanolamine, n-pentylamine, s-pentylamine, isopentylamine, 2-pentanolamine, 3-pentanolamine, 4-pentanolamine, 5-pentanolamine, n-hexylamine, s-hexylamine, isohexylamine, cyclohexylamine, 2-hexanolamine, 3-hexanolamine, 4-hexanolamine, 5-hexanolamine, 6-hexanolamine, toluidine or aniline The term "secondary amine" within the context of the present application means a molecule which is capable of acting as an aminating agent and having the formula NHR'R", wherein the residues R' and R" can be identical or different from each other and can each be independently selected from linear or branched alkyl groups, linear or branched alkanol groups, cyclic alkyl groups which may be substituted and aromatic groups which may be substituted. Further, the residues R' and R" can form together with the nitrogen atom to which the residues R' and R" are attached a heterocyclic alkyl group or a heterocyclic aromatic group, like piperidine, pyrrolidine, morpholine, piperazine.

In particular, residues R' and R" can be independently from each other selected from methyl, ethyl, ethanol, n-propyl, iso-propyl, propanol, iso-propanol, propane-1,2-diol, n-butyl, sec-butyl, iso-butyl, 2-butanol, 3-butanol, 4-butanol, n-pentyl, sec-pentyl, iso-pentyl, 2-pentanol, 3-pentanol, 4-pentanol, 5-pentanol, n-hexyl, sec-hexyl, iso-hexyl, cyclohexyl, 2-hexanol, 3-hexanol, 4-hexanol, 5-hexanol, 6-hexanol, toluyl or phenyl.

Examples of secondary amines suitable to be used in the methods according to the invention can be selected from dimethylamine, methylethylamine, diethylamine, N-methyl-2-ethanolamine, N-ethyl-2-ethanolamine, N-propyl-2-ethanolamine, N-butyl-2-ethanolamine, N-pentyl-2-ethanolamine, N-hexyl-2-ethanolamine, di-2-ethanolamine, dinpropylamine, di-s-propylamine, diisopropylamine, isopropylmethylamine, isopropylethylamine, N-methyl-2-propanolamine, N-methyl 3-propanolamine, dipropanolamine, di-n-butylamine, di-s-butylamine, diisobutylamine, N-methyl-2-bu-tanolamine, N-methyl-3-butanolamine, N-methyl-4-butanolamine, N-ethyl-2-butanolamine, N-ethyl-3-butanolamine, N-ethyl-4-butanolamine, N-propyl-2-butanolamine, N-propyl-3-butanolamine, N-propyl-4-butanolamine, N-butyl-2-butanolamine, N-butyl-3-butanolamine, N-butyl-4-butanolamine, di-2-butanolamine, di-3-butanolamine, di-4-butanolamine, di-n-pentylamine, di-s-pentylamine, diisopentylamine, N-methyl-5-pentanolamine, N-ethyl-5-pentanolamine, N-propyl-5-pentanolamine, N-butyl-5-pentanolamine, N-pentyl-5-pentanolamine, di-2-pentanolamine, di-3-pentanolamine, di-4-pentanolamine, di-5-pentanolamine, di-n-hexylamine, di-s-hexylamine, diisohexylamine, N-methyl-2-hexanolamine, N-methyl-3-hexanolamine, N-methyl-4-hexanolamine, N-methyl-5-hexanolamine, N-methyl-6-hexanolamine, N-ethyl-2-hexanolamine, N-ethyl-3-hexanolamine, N-ethyl-4-hexanolamine, N-ethyl-5-hexanolamine, N-ethyl-6-hexanolamine, N-propyl-2-hexanolamine, N-propyl-3-hexanolamine, N-propyl-4-hexanolamine, N-propyl-5-hexanolamine, N-propyl-6-hexanolamine, N-butyl-2-hexanolamine, N-butyl-3-hexanolamine, N-butyl-4-hexanolamine, N-butyl-5-hexanolamine, N-butyl-6-hexanolamine, N-pentyl-2-hexanolamine, N-pentyl-3-hexanolamine, N-pentyl-4-hexanolamine, N-pentyl-5-hexanolamine, N-pentyl-6-hexanolamine, N-hexyl-6-hexanolamine, di-2-hexanolamine, di-3-hexanolamine, di-4-hexanolamine, di-5-hexanolamine, di-6-hexanolamine, piperidine, pyrrolidine, piperazine or morpholine.

The term "carbon percent yield (C %)" within the context of the present application means the yield of (by)product(s) which can be calculated by dividing the number of moles of carbon derived from the residue of glycolaldehyde in the (by)product in the reaction mixture, by the total number of moles of carbon supplied to the reaction via the glycolaldehyde educt. The carbon atoms that originate from the at least one primary and/or secondary amine are not taken into account for the yield determination.

The term "supported hydrogenation catalyst" within the context of the present application is defined as follows:

Sometimes in literature supported hydrogenation catalysts are also called bifunctional hydrogenation catalysts due to the presence of an acid/base functionality provided by the support part of the catalyst and the property to activate hydrogen due to the metal part of the catalyst. In any case, the respective catalyst possesses hydrogenation capacity towards a substrate. In the methods according to the invention, the supported hydrogenation catalyst used shows hydrogenation capacity towards glycolaldehyde—amine adducts and fragments thereof. The supported hydrogenation catalyst used in the methods according to the invention has to be distinguished from unsupported hydrogenation catalysts (also referred to in the literature as monofunctional hydrogenation catalysts), in particular from hydrogenation catalysts of the Raney-type, e.g. Raney Nickel or spongy hydrogenation catalysts, e.g. spongy nickel.

Supported hydrogenation catalysts which are suitable to be used in the methods according to the invention comprise, respectively consist of a metal part and a support part.

The metal part of the supported hydrogenation catalyst consists of at least one metal. This at least one metal has the property to activate hydrogen in order to facilitate the hydrogenation of glycolaldehyde, and therefore is present, at least to some extent, in the zero ("0") oxidation state under the operating conditions and can be regarded as catalytic active metal center. The at least one metal is preferably selected from copper, nickel, cobalt, iron, ruthenium, platinum, palladium, or two or more thereof. In case two or more metals are present in the supported hydrogenation catalyst, these two or more metals can be present in form of an alloy; these two or more metals can exist next to each other in separate so-called crystallites without forming an alloy or the like; or these two or more metals can be present in metal crystallites consisting of zones of each individual metal without forming an alloy or the like (e.g. the metal crystallites can consist of layers of the individual metals.)

The support part of the hydrogenation catalyst comprises or consists of at least one support substrate for the at least one catalytic active metal center of the metal part of the supported hydrogenation catalyst. The at least one metal is located on the surface of the support substrate. The support substrate preferably embeds the at least one metal. The at least one support substrate can be carbon, a polymer or a (mixed) metal oxide. A carbon support can be an activated carbon (AC), obtained from a suitable natural material such as peat, wood, coconut husk, nut shells, lignite etc.; a modified activated carbon (e.g. by oxidation steaming or sulfonation); graphite or synthetic carbon nanotubes. A polymer support substrate can be poly (acrylic acid), polystyrene, poly (styrene-co-divinylbenzene), or polyamides. A metal oxide support substrate can be silica ($SiO_2$); alumina ($Al_2O_3$); or silica-alumina mixture ($SiO_2/Al_2O_3$), either in an amorphous form or in a crystalline form (e.g. zeolites); $TiO_2$; $ZrO_2$. Further, the metal oxide support can also be the oxide of one of the catalytic active metals as defined above. The catalytic active metal center of the supported hydrogenation catalyst can hence be generated by partial reduction of the metal oxide in the supported hydrogenation catalyst, leaving sufficient metal oxide substrate to support the catalytic active metal center.

Synthesis of catalyst precursors and subsequent generation of the active catalyst through reduction (and additional passivation) is a well-known conventional practice by a man skilled in the art (for example P. Kluson, 1994, Preparation and properties of Ruthenium supported catalysts, Catalysis Letters, Vol. 23, p 299-312). The catalyst precursor can for example be prepared by, but not limited to, known processes such as (co-)precipitation or impregnation, generally followed by a calcination to obtain the catalyst precursor, commonly obtaining the metal in its oxide form. Reduction of the catalyst precursor can then be performed at elevated temperatures in a moving or stationary reduction oven, with a reduction agent being typically hydrogen or a hydrogen-comprising gas, to obtain the catalyst in its active form. Another method of catalyst precursor reduction can be performed in suspension, for example in a stirred autoclave.

Examples of supported hydrogenation catalysts suitable to be used in the methods according to the invention can be selected from, but are not limited to, Ni-6458P (BASF); Ni-5249P (BASF), Ni-3354E (BASF), Ni/$SiO_2$—$Al_2O_3$ (65 wt % Ni, Sigma-Aldrich), Pd/C (5 wt % Pd, Sigma-Aldrich) or Ru/C (5 wt % Pd, Sigma-Aldrich). These catalysts were already supplied by the manufacturer in a reduced and passivated form.

The term "hydrogen" within the context of the present application means elementary hydrogen $H_2$. The hydrogen is used in the methods according to the invention in gaseous form.

The term "reaction mixture" within the context of the present application means a mixture of at least glycolaldehyde and ammonia and/or primary and/or secondary amine. The reaction mixture can further contain the at least one supported hydrogenation catalyst and/or a reactive fluid for instance a reactive solvent, like methanol, which was also used for dissolving e.g. glycolaldehyde and/or ammonia and/or the at least one primary amine and/or the at least one secondary amine and/or intermediate products of the reaction and/or end products of the reaction and/or byproducts of the reaction. The supported hydrogenation catalyst can be already present in the reaction mixture in the first step, or can be added to the reaction mixture at the beginning of the second step.

The reaction mixture can be either a homogeneous reaction mixture, e.g. a solution or a heterogeneous reaction mixture, e.g. a suspension or a dispersion. Further, the reaction mixture can also contain hydrogen, either in gaseous form or the hydrogen can be at least partly dissolved in e.g. the liquid components of the reaction mixture. The reaction mixture contains hydrogen only after step 1 is completed; i.e. only as early as step 2 is conducted.

The process according to the invention is typically performed at a pressure of 1 to 150 bar. The pressure is maintained or controlled generally via the metered addition of nitrogen and/or hydrogen or a mixture thereof.

The term "reaction pressure" within the context of the present application means the pressure which is used, respectively which is applied to the reaction mixture prior to start heating the reaction mixture to the reaction temperature. The temperature of the reaction mixture when the reaction pressure is applied can be between 10° C. to 30° C., but is usually the same temperature as the ambient temperature. The temperature of the reaction mixture when the reaction pressure is applied can be also higher than ambient temperature if e.g. pre-heated educts or a pre-heated reaction mixture is used. The reaction pressure has to be distinguished from the pressure during the reaction. The reaction pressure can be e.g. applied to the reaction mixture by filling in gases like nitrogen or hydrogen into the reaction vessel until the desired reaction pressure is achieved.

The term "pressure during the reaction" within the context of the present application means the pressure which can be observed when heating of the reaction mixture is started, respectively if the temperature of the reaction mixture is further increased.

The term "reaction temperature" within the context of the present application means the temperature to which the reaction mixture is heated (maybe also called "reaction temperature set point") and which is maintained until completion of the reaction.

The term "reaction time" within the context of the present application depends on the manner on how the methods according to the invention are performed The term "batchwise manner", respectively "batchwise" within the context of the present application and its conventional use means that at least some necessary educts, like glycolaldehyde are loaded into the reaction vessel prior to the actual reaction taking place, the reaction vessel is then closed and pressurized.

The term "fed-batch manner", respectively "fed-batch" within the context of the present application and its conventional use means that the reaction vessel is at least partly filled with educts at the start; or at least filled with one of the educts. The reactor is then closed and heating is started. Then, if the reaction temperature set point is reached, further educt(s) (either more of those that were initially present, or new ones) are supplied (also called "fed") into the reaction vessel until e.g. the maximum filling capacity of the reaction vessel is achieved, or the maximum duration of the experiment (e.g. end of the working day) is achieved. In a fed batch run, no reaction mixture or product mixture is removed from the reactor during the run. Only after the reaction is completed, the product (mixture) is discharged from the reaction vessel and the reaction vessel can be either cleaned if necessary, or filled again with educts.

In one embodiment, the polar organic protic fluid is selected from C1-C4-alkahols, acetic acid, formic acid, and mixtures thereof. An exemplary mixture is ethanol/acetic acid. In one preferred embodiment, the protic fluid is acetic acid. In another preferred embodiment, the protic fluid is selected from C1-C4-alkanols and mixtures thereof. In a more preferred embodiment, the protic fluid is methanol or ethanol or isopropanol. In a particularly preferred embodiment, the protic fluid is methanol.

Terahydrofuran (THF) or (CH2)4O is an aprotic organic heterocyclic liquid, specifically a cyclic ether, of low relative polarity of 0.207 (A value for relative polarity as normalized from measurements of fluid shifts of absorption spectra and were extracted from Christian Reichardt, Fluids and Fluid Effects in Organic Chemistry, Wiley-VCH Publishers, 3rd ed., 2003).

The solvent polarity index of a fluid of specific compounds, for instance the polar protic organic fluid of present invention, can be measured in accordance with D. Harris, Quantitative Chemical Analysis, 9th ed., 2015. & E. Katz et al., Eds., Handbook of HPLC, Marcel Dekker, New York, 1998. The values of relative polarity of a fluid of specific compounds, for instance the polar protic organic fluid of present invention can be are normalized from measurements of solvent shifts of absorption spectra in accordance with Christian Reichardt, Solvents and Solvent Effects in Organic Chemistry, Wiley-VCH Publishers, 3rd ed., 2003). The values of dielectric constant, κ, a ration, of a fluid of specific compounds, for instance the polar protic organic fluid of present invention can be measured for static electric fields as follows: first the capacitance of a test capacitor, Co, is measured with vacuum between its plates. Then, using the same capacitor and distance between its plates the capacitance $C_x$ with a dielectric between the plates is measured. The dieletric constant, κ is defined by this ration: $\kappa = C_x/C_0$ The polar protic organic fluid of present invention preferably have a high dielectric constant, for example, a dielectric constant of greater than or equal to 15 or 15 to 45 or to about 45, or a dielectric constant of 20 or 90 or from about 20 to about 90, e.g. from about 20 or about 80 or 20 to 80 (e.g., at or about, or at least at or about 20, 21, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, or 81) and high polarity index, for instance a polarity index of from about 4,5 or from about 4,5 to 9, or to about 9, and preferably they have a dipole moment of between 1.65 to 2.8. Furthermore the polar fluids preferably have large dipole moment, for example a dipole moment that is greater than 1.4 Debye or about 1.4 Debye, such as at or about 1.4 Debye, 1.5 Debye, 1.6 Debye, 1.7 Debye, 1.8 Debye, 1.9 Debye, 2.0 Debye, 2.1 Debye, 2.2 Debye, 2.3 Debye, 2.4 Debye, 2.5 Debye, 2.6 Debye, 3.0 Debye, 3.5 Debye, larger than 4 Debye or 4 Debye.

In one embodiment, the polar protic organic fluid of present invention has a dielectric constant that is larger than 15 or a dielectric constant of between 15 and 50, and typically from between 25 or about 45. In another embodiment, the polar protic organic fluid polarity index is from 3 or from about 3 or to 9 or to about 9. In another embodiment, the dipole moment of the polar protic organic fluid is from 1.5 to 3, and usually from about 1.8 or 1.8 to 2.8, e.g. 1.9, 2.6 and 2.2 (dielectric constant of the solvent see e.g. Landolt-Bornstein, New SeriesIV/17, Static Dielectric constants of Pure Liquids and Binary Liquid Mixtures, Springer, 2008; and CRC Handbook of Chemistry and Physics, "Lide editor, edition 82, CRC Press, 2001; the solvent dipole moment, see for example CRC Handbook of Chemistry and Physics, "Lide editor, edition 82, CRC Press, 2001; and the polarity index for solvents, see, for example, Snyder," Classification of the solvent properties of common liquids,' J. Chromatography A, 92: 223-230, 1974).

According to an aspect of the present invention there is provided a process for the preparation for producing (N-substituted) alkanolamines and diamines by reaction of glycolaldehyde with an aminating agent, the process characterized in that it is a two-step method with step 1) reacting glycolaldehyde and ammonia NH3 or at least one primary amine NH2R or at least one secondary amine NHR'R" in the presence of or contacting a reactive organic fluid in a first step, to give unsaturated intermediates, and step 2) reacting the reaction mixture obtained in the first step with hydrogen further characterized in that the in reaction mixture contacts a solid catalyst and still in the presence of a organic fluid. With respect to the formation of unsaturated intermediates in the first step, it is noted that it is advantageous if this reactive organic fluid participates in the reaction by facilitating proton transfers. At least part of molecules of the organic fluid preferably contain a labile H+ or have an acidic, eventually weak acidic hydrogen. This is particularly the case if the reactive organic fluid is a protic organic fluid which comprises molecules with a hydrogen atom bound to an oxygen (as in a hydroxyl group) or bound to an nitrogen (as in an amine group). And preferably the organic fluid is polar and has an high dielectric constant (dielectric constant of greater than or equal to 15) and high polarity (polarity index (P) above 5 and/or relative polarity above 0.400). By using this inventive system it is possible operate this process with higher yields compared to aprotic solvents or water. Some of the techniques described above may be embodied as a two-step one-pot process. In an embodiment of the invention, the reactive organic fluid has a dielectric constant of a value between 15 to 50 or of a value between 25 to 45 or of a value between 20 or 90. In yet an embodiment of the invention, the reactive organic fluid has a dipole moment that is larger than 1.4 Debye or that is larger than 1.5 Debye. In an embodiment of the invention, the reactive organic fluid has a polarity index is of a value between 3 to 9 or a polarity index is of a value between 1.8 to 2.

According to an aspect of the present invention there is provided a process for the preparation for producing (N-substituted) alkanolamines and diamines by reaction of glycolaldehyde with an aminating agent, the process characterized in that it is a two-step method with step 1) reacting glycolaldehyde and ammonia NH3 or at least one primary amine NH2R or at least one secondary amine NHR'R" in the presence of or contacting a reactive organic fluid in a first step, to give unsaturated intermediates, and step 2) reacting the reaction mixture obtained in the first step with hydrogen further characterized in that the in reaction mixture contacts a solid catalyst and still in the presence of a protic organic fluid. With respect to the formation of unsaturated intermediates in the first step, it is noted that it is advantageous that the organic fluid or at least part of its molecules readily participate in the reaction by donate protons (H+). At least part of molecules of the organic fluid preferably contain a labile H+ or have an acidic, eventually weak acidid hydrogen. This is particularly the case if the organic fluid is a protic organic fluid catalyst comprises molecules with O—H or N—H bonds serving as a source of protons (H+). And preferably the organic fluid is polar and has an high dielectric constant (dielectric constant of greater than or equal to 15) and high polarity (polarity index (P) above 5 and/or relative polarity above 0.400). By using this inventive system it is possible operate this process with higher yields compared to aprotic solvents or water. Some of the techniques described above may be embodied as a two-step one-pot process. In an embodiment of the invention, the protic organic fluid catalyst has a dielectric constant of a value between 15 to 50 or of a value between 25 to 45 or of a value between 20 or 90. In an embodiment of the invention, the protic organic fluid catalyst has a dipole moment that is larger than 1.4 Debye or larger than 1.5 Debye. In an embodiment of the invention, the protic organic fluid catalyst has a polarity index is of a value between 3 to 9 or a polarity index is of a value between 1.8 to 2.

According to an aspect of the present invention there is provided a process for the preparation for producing (N-substituted) alkanolamines and diamines by reaction of glycolaldehyde with an aminating agent, the process characterized in that it is a two-step method with step 1) reacting glycolaldehyde and ammonia NH3 or at least one primary amine NH2R or at least one secondary amine NHR'R" in the presence of or contacting a reactive organic fluid in a first step, to give unsaturated intermediates, and step 2) reacting the reaction mixture obtained in the first step with hydrogen further characterized in that the in reaction mixture contacts a solid catalyst and still in the presence of a polar protic organic fluid. With respect to the formation of unsaturated intermediates in the first step, it is noted that it is advantageous that the organic fluid or at least part of its molecules readily participate in the reaction by donate protons (H+). This is particularly the case if the organic fluid is polar protic organic fluid comprises molecules with O—H or N—H bonds serving as a source of protons (H+). And preferably the organic fluid is polar and has an high dielectric constant (dielectric constant of greater than or equal to 15) and high polarity (polarity index (P) above 5 and/or relative polarity above 0.400). By using this inventive system it is possible operate this process with higher yields compared to aprotic solvents or water. Some of the techniques described above may be embodied as a two-step one-pot process. In an embodiment of the invention, the protic organic fluid catalyst has a dielectric constant of a value between 15 to 50 or of a value between 25 to 45 or of a value between 20 or 90. In yet an embodiment of the invention, the protic organic fluid catalyst has a dipole moment that is larger than 1.4 Debye or that is larger than 1.5 Debye. In yet an embodiment of the invention, the protic organic fluid catalyst has a polarity index is of a value between 3 to 9 or that is of a value between 1.8 to 2.

Yet another particular embodiment concerns one-pot two-step process for producing (N-substituted) alkanolamines and diamines by reaction of glycolaldehyde with an aminating agent, which process comprises the two steps: 1) reacting glycolaldehyde and ammonia $NH_3$ or at least one primary amine $NH_2R$ or at least one secondary amine NHR'R" in the presence of or contacting a reactiveorganic fluid in a first step, to give unsaturated intermediates, whereby the organic solvent comprises the reaction mixture of step one as a solute and whereby the organic solvent is composed of or comprises molecules that readily donate protons ($H^+$) to reagents of the reaction mixture, and 2) reacting the reaction mixture obtained in step 1) with hydrogen and in the presence of a solid catalyst or contacting a solid catalyst and still in the presence of a organic fluid.

With respect to the formation of unsaturated intermediates in the first step, it is noted that it is advantageous if this organic solvent participates in the hydrogenation reaction by hydrogen bonding. At least part of molecules of the organic solvent preferably contain a labile H+ or have an acidic, eventually weak acidic hydrogen. This is particularly the case if the organic solvent is a protic organic solvent which comprises molecules with a hydrogen atom bound to an oxygen (as in a hydroxyl group) or bound to an nitrogen (as in an amine group) or which comprises or is composed of molecules with labile proton like a hydroxyl proton or carboxylic acid proton or a molecule that has a hydrogen atom bonded to an electronegative atom, yielding highly polarized bonds in which the hydrogen has protonlike character and can have hydrogen bonding characteristics.

And preferably the solvent is polar and has an high dielectric constant (dielectric constant of greater than or equal to 15) and high polarity (polarity index (P) above 5 and/or relative polarity above 0.400). By using this inventive system it is possible operate this process with higher yields compared to aprotic solvents or water. Some of the techniques described above may be embodied as a two-step one-pot process. In an embodiment of the invention, the reactive organic solvent has a dielectric constant of a value between 15 to 50 or of a value between 25 to 45 or of a value between 20 or 90. In yet an embodiment of the invention, the reactive organic solvent has a dipole moment that is larger than 1.4 Debye or that is larger than 1.5 Debye. In an embodiment of the invention, the reactive organic solvent has a polarity index is of a value between 3 to 9 or a polarity index is of a value between 1.8 to 2.

Yet another particular embodiment concerns a method for producing (N-substituted) alkanolamines and diamines by reaction of glycolaldehyde with an aminating agent in a two-step method and in the presence of reactive organic fluid or the organic solvent contacting the reagents whereby the organic fluid comprises or is composed of polar protic organic solvent and in the presence of a solid catalyst or contacting a solid catalyst, whereby the polar protic organic solvent is composed of molecules with 1 to 4 C atoms, whereby this two-step method is a one-pot method that comprises as two steps: 1) reacting glycolaldehyde and ammonia $NH_3$ or at least one primary amine $NH_2R$ or at least one secondary amine NHR'R" in the presence of or contacting a reactive organic fluid in a first step, to give unsaturated intermediates, and 2) in the second step reacting the reaction mixture obtained in step 1) with hydrogen and a solid catalyst or contacting a solid catalyst whilst still in the presence of the organic fluid. With respect to the formation of unsaturated intermediates in the first step, it is noted that it is advantageous if this polar protic organic solvent participates in the hydrogenation reaction by hydrogen bonding. At least part of molecules of the polar protic organic solvent preferably contain a labile H+ or have an acidic, eventually weak acidic hydrogen. This is particularly the case if the polar protic organic solvent is a protic polar protic organic solvent which comprises molecules with a hydrogen atom bound to an oxygen (as in a hydroxyl group) or bound to an nitrogen (as in an amine group) or which comprises or is composed of molecules with labile proton like a hydroxyl proton or carboxylic acid proton or a molecule that has a hydrogen atom bonded to an electronegative atom, yielding highly polarized bonds in which the hydrogen has protonlike character and can have hydrogen bonding characteristics. And preferably the solvent is polar and has an high dielectric constant (dielectric constant of greater than or equal to 15) and high polarity (polarity index (P) above 5 and/or relative polarity above 0.400). By using this inventive system it is possible operate this process with higher yields compared to aprotic solventsor water. Some of the techniques described above may be embodied as a two-step one-pot process. In an embodiment of the invention, the reactive polar protic organic solvent has a dielectric constant of a value between 15 to 50 or of a value between 25 to 45 or of a value between 20 or 90. In yet an embodiment of the invention, the reactive polar protic organic solvent has a dipole moment that is larger than 1.4 Debye or that is larger than 1.5 Debye. In an embodiment of the invention, the reactive polar protic organic solvent has a polarity index is of a value between 3 to 9 or a polarity index is of a value between 1.8 to 2.

Preferably the two-step process of present invention is a one-pot process.

A particular embodiment of the invention advantageously comprises that reaction of glycolaldehyde with an aminating agent in the presence of hydrogen and a catalyst takes place in an organic solvent that comprises the reagents as solute and that acts as a co-catalyst in the formation of imines and enamines. Preferred solvents are polar protic solvents, preferably alcohols, such as methanol, ethanol or 2-propanol, and diols such as ethylene glycol, or mixtures thereof.

The method according to the invention provides the advantage that (N-substituted) alkanolamines and diamines can be produced without using water. The method according to the invention furthermore provides the advantage that (N-substituted) alkanolamines and diamines can be produced in high yields and tunable selectivity. Without wanting to be bound to any theory, the inventors assume that the presence of the organic fluid or the solvent of present invention enables to control the selectivity of the reaction by assisting the effects of certain process conditions such as the amine-to-glycolaldehyde ratio. As such, both reaction steps can advantageously be affected in one reactor chamber, in the most optimal set of conditions for each step, leading to minimal side reactions.

In aspect, the present invention provides that (N-substituted) alkanolamines and diamines are produced by the method according to the invention in yields of at least 30 C %, preferably at least 35 C %, preferably at least 40 C %, preferably at least 45 C %, preferably at least 50 C %, preferably at least 55 C %, more preferably at least 60 C %, more preferably at least 65 C %, more preferably at least 70 C %, more preferably at least 75 C %, more preferably at least 80 C %, more preferably at least 85 C %, more preferably at least 90 C % and more based on the total amount of glycolaldehyde used as educt. Yields are expressed in carbon percent (C %) unless otherwise stated.

In particular aspect, the present invention, products obtained by the method according to the invention can be, but are not limited to (N-substituted) alkanolamines and diamines, such as monoethanolamine (MOEA), diethanolamine (DEOA), triethanolamine (TEOA), ethylenediamine (EDA), 2-(methylamino)ethanolamine (MAE), N-methyldiethanolamine (MDEA), N,N'-dimethylethylenediamine (DMEDA), 2-dimethylamino)ethanolamine (DMAE), N,N,N',N'-tetramethylethylenediamine (TMEDA). Further, the methods according to the invention have the advantage that the formation of heterocyclic by-products like N-alkylated piperazines, C-alkylated piperazine or unsubstituted piperazines can be reduced, preferably minimized. Preferably at most 10 C %; further preferably at most 9 C %, further preferably at most 8 C %, further preferably at most 7 C %, further preferably at most 6 C %, further preferably at most 5 C %, further preferably at most 4 C %, more preferred at most 3 C %, even more preferred at most 2 C %, even more preferred at most 1 C % of heterocyclic by-products are formed based on the total amount of glycolaldehyde used as educt. Such heterocyclic by-products formed may be cyclic ethylene diamine derivatives like N-alkylated piperazines, C-alkylated piperazines, N-alkylated C-alkylated piperazines or unsubstituted piperazine.

According to an aspect of the present invention there is provided that in the process according to the invention, glycolaldehyde is used. It can either be used as an starting educt of the reaction, or as an intermediate derived from carbohydrates of which the formation can be exploited in the first step of the reaction procedure. It is commercially available and can be prepared by oxidizing ethylene glycol (see JP3246248 and JP3279342), or by reaction of formaldehyde with carbon monoxide and hydrogen (see U.S. Pat. Nos. 7,511,178B2, 7,420,093B2, 7,449,607B2 and EP1697291). Glycolaldehyde is preferably synthesized from biomass feedstocks, such as the hydrous thermolysis of carbohydrates (see U.S. Pat. No. 7,094,932B2, WO2014131764A1). The substrate can be used in solid form, as a gaseous feed or in form of a solution, wherein glycolaldehyde is dissolved in at least one solvent or a mixture thereof.

A further starting material used in the process according to the invention is an aminating agent. The aminating agents used in the reductive amination of alcohols, aldehydes or ketones in the presence of hydrogen may be either ammonia or primary or secondary aliphatic or cycloaliphatic or aromatic amines. The aminating agent is preferably a nitrogen compound of the formula:

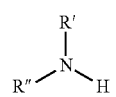

In which R' and R" can be each independently selected from hydrogen (H), linear or branched alkyl groups, linear or branched alkanol groups, cyclic alkyl groups which may be substituted and aromatic groups, which may be substituted.

In general, at least one primary amine or at least one secondary amine or at least ammonia or a mixture of at least one primary amine and at least one secondary amine and ammonia can be used in the method according to the invention. In one embodiment of the methods according to the invention only ammonia is reacted with glycolaldehyde and hydrogen. In one embodiment of the methods according to the invention only one primary amine is reacted with glycolaldehyde and hydrogen. In one embodiment of the methods according to the invention two or more, e.g. three or four primary amines are reacted with glycolaldehyde and hydrogen. In one embodiment of the method according to the invention only one secondary amine is reacted with glycolaldehyde and hydrogen. In one embodiment of the method according to the invention two or more, e.g. three or four secondary amines are reacted with glycolaldehyde and hydrogen. In case a mixture of at least ammonia and at least one primary amine and at least one secondary amine is used in the method according to the invention, no restriction with respect to the molar ratios between the ammonia and the at least one primary amine and the at least one secondary amine need to be considered.

The ammonia and/or at least one primary amine and/or the at least one secondary amine can be used in gaseous form. The ammonia and/or at least one primary amine and/or secondary amine can be also used in liquid form. The ammonia and/or at least one primary amine and/or one secondary amine can be also used in form of a solution, wherein the ammonia and/or at least one primary amine and/or the at least one secondary amine is dissolved in protic organic solvent or protic organic solvent mixture. Suitable organic solvents are polar protic organic solvents such as methanol, ethanol, ethylene glycol, methylaminoethanol or dimethylaminoethanol. The ammonia and/or at least one primary amine and/or the at least one secondary amine can be used in solid form, e.g. in form of a salt.

The method according to the invention generally proceeds at a molar amine-to-substrate molar ratio of ammonia and/or the at least one primary amine and/or secondary amine of 1/3 to 40/1

In a particular embodiment of the present invention, the method proceeds at a stoichiometric amine-to-substrate molar ratio of ammonia and/or the at least one primary amine and/or secondary amine, according to the obtained final product. For instance, ammonia needs to react three times with glycolaldehyde in order to produce triethanolamine, thus a molar ratio of 1/3. As such, high product selectivities can be achieved whilst minimizing side-reactions.

One further advantage of the method according to the invention is that the use of a supported hydrogenation catalyst results in high yields and purity of the obtained products. In particular, the formation of by-products like heterocyclic compounds like piperazines or derivatives thereof, can be minimized by using the supported hydrogenation catalyst in the methods according to the invention.

In a particular embodiment of present invention, the supported hydrogenation catalyst consists of one metal and one support substrate. Such as supported hydrogenation catalyst can be selected from supported nickel hydrogenation catalysts and particularly preferable is a supported hydrogenation catalysts of the group consisting of Pd/C and Ru/C. In one embodiment, the supported hydrogenation catalyst consists of two or more metals and two or more support substrates. The supported hydrogenation catalyst can be directly added to the reaction mixture in solid form, e.g. as a powder. In such a case, the supported hydrogenation catalyst is suspended in the liquid reaction medium by a suitable way of agitation, for instance an axial stirrer or a circulation pump. The supported hydrogenation catalyst can be separated from the reaction medium after the reaction has been completed e.g. by filtration, centrifugation or settlement. The amount of the supported catalyst added to the reaction depends on the total amount of liquids present in the reaction mixture in order to maintain stirrability, respectively pumpability of the reaction mixture. Generally the amount of supported catalyst can be up to 30 weight %, or up to 25 weight %, or up to 25 weight %, or up to 20 weight %, or up to 15 weight %, or up to 10 weight %, or up to 7 weight %, or up to 5 weight %, or up to 3 weight %, or up to 1 weight %.

Alternatively, the supported hydrogenation catalyst can be fixed in the reactor while the reaction mixture, consisting of liquids and/or gases, is circulated over the fixed catalyst bed. The fixed catalyst bed can for instance be supported into a tubular reactor and the reaction mixture is equally distributed over the cross section of the tube to assure optimal contact of the reaction medium and the catalyst particles. The reactor can be filled with either one bed of catalyst particles, but also consecutive beds of catalyst can be placed into the tubular reactor, optionally with liquid and/or gas distributers between some or all of the beds. To allow the supported hydrogenation catalyst to be packed in a bed and at the same time leaving sufficient freedom for the reaction mixture to pass, the supported hydrogenation catalyst may be in a powderous form. Preferably the supported hydrogenation catalyst is "formed" into a suitable catalyst particle. Such particle can be of cylindrical, spherical, bilobe, trilobe or any other suitable shape, but can also be in the shape of a monolith, allowing the reaction medium to flow past and through it. Forming of catalyst particles can be done by any conventional method such as pelletizing, tableting, spray drying, extrusion, granulating, etc. The reaction mixture can move either from top to bottom over the catalyst bed, or from bottom to top. Gas and liquid streams can either be in the same direction (co-current) or in opposite direction (counter-current). Circulation can be in a way that the reaction mixture passes the fixed catalyst bed only once (once through) or that is circulated multiple times over the fixed catalyst bed. Product withdrawal from the circulation stream can be either continuous or all at once at the end of the reaction after a predefined time of circulation.

The reaction pressure used in the methods according to the invention is superatmospheric pressure which means any pressure which is higher than the standard ambient pressure of 1 bar. In particular, the reaction pressure used in the methods according to the invention is at least 10 bar, or at least 30 bar, or at least 50 bar, or at least 60 bar, or at least 70 bar, or at least 100 bar, or at most 110 bar, or at most 120 bar, or at most 130 bar, or at most 140 bar, or at most 150 bar, or at most 160 bar, or at most 170 bar, or at most 180 bar, or at most 190 bar, or at most 200 bar. Preferably, the reaction pressure is at least 10 bar and at most 200 bar, preferably at least 50 bar and at most 150 bar, preferably 70 bar. Also reaction pressures of above 200 bar are possible. The upper limit of the reaction pressure is determined by the equipment used.

When the reaction is performed in a closed vessel, the pressure increases due to thermal expansion of the compounds present in the reaction mixture during heating of the reaction mixture up to the reaction temperature set point.

Thus, the pressure during the reaction is at least for a certain time higher than the reaction pressure prior to the start of heating the reaction mixture. The pressure during the reaction raises up to a maximum value. This maximum value of the pressure during the reaction depends on the set-up, geometry and filing degree of the reaction vessel. Further, when heating is started, respectively if the temperature of the reaction mixture is further increased, the components within the reaction vessel start to react with each other. This means that hydrogen is consumed. In case of a two-step procedure, hydrogen consumption takes place in step 2. Hydrogen consumption (and in some embodiments depending on the ammonia and/or at least one primary and/or secondary amine used also the consumption of volatile primary and/or secondary amine), however, leads to a decrease of the pressure during the reaction. Thus, two contrary effects influence the pressure during the reaction at the same time until reaction is complete: 1. Thermal expansion of the components of the reaction mixture due to heating result in an increase of the pressure during the reaction and 2. Consumption of hydrogen (and in some embodiments depending on the ammonia and/or at least one primary and/or secondary amine used also the consumption of volatile primary and/or secondary amine) due to reaction with the other components present in the reaction mixture lead to a decrease of the pressure during the reaction. When heating is started, respectively if the temperature of the reaction mixture is further increased, the thermal expansion is the predominating effect and therefore the pressure during the reaction increases up to a maximum value. Then, the consumption of hydrogen (and in some embodiments depending on the ammonia and/or at least one primary and/or secondary amine used also the consumption of volatile ammonia and/or primary and/or secondary amine) becomes the predominating effect and therefore, a decrease of the pressure during the reaction can be observed, although heating is not switched of, respectively is still ongoing. If the pressure during the reaction starts to decrease, this shows that reaction takes place inside the reaction vessel and glycolaldehyde, ammonia and/or primary amine and/or secondary amine and hydrogen are reacted at least partly to (N-substituted) alkanolamines and diamines.

After a certain reaction time, the pressure during the reaction neither decreases any further, nor increases again; a constant value of the pressure during the reaction can be observed. If the pressure during the reaction does not change any more, this signals that the reaction is complete. If now e.g. heating is switched off, then of course a further decrease of the pressure can be observed since the whole product (mixture) cools down. This pressure change might be then referred to as "pressure after the reaction", since the reaction is already completed.

In case of a two-step procedure, the first step and second step can be performed in two different reaction vessels. Thus, the pressure decrease due to hydrogen consumption can only be observed in the reaction vessel used for the second step. Further, it is also possible to include a cooling step between the end of the first step and the beginning of the second step, independently from performing the first and the second step in one reaction vessel or two different reaction vessels. Therefore it is possible to observe a pressure decrease between the first and the second step due to temperature decrease.

One further advantage of the methods according to the invention is that the methods can be conducted under mild reaction temperature without negative influence on the yield and purity of (N-substituted) alkanolamines and/or diamines obtained as product(s).

The process according to the invention generally proceeds at temperatures of 15 to 250° C. The reaction mixture can be heated up to the reaction temperature set point e.g. under stirring.

During the heating phase, the temperature can overshoot the reaction temperature set point and then the temperature is lowered until the desired reaction temperature set point is achieved.

The reaction temperature, respectively the reaction temperature set point used in the methods according to the invention is at least 50° C., or at least 75° C., or at least 100° C., or at least 110° C., or at least 120° C., or at least 130° C., or at least 140° C., or at least 150° C., or at most 160° C., or at most 170° C., or at most 180° C., or at most 190° C., or at most 200° C. Preferably, the reaction temperature is at least 50° C. and at most 200° C., preferably at least 100° C. and at most 150° C.

In case the methods according to the invention are performed in a batchwise manner in a closed reaction vessel, the reaction time is the time range starting when the heating of the reaction mixture is started, respectively switched on and the point in time when a constant value of the pressure during the reaction is observed for the first time, i.e. the reaction is completed. If a constant pressure value is observed, the reaction can either be immediately stopped or can be allowed to rest at the reaction conditions for some further time. This time, however, then also accounts to the reaction time. In particular, the reaction time can be at least 1 minute, or at least 5 minutes, or at least 10 minutes, or at least 15 minutes, or at least 20 minutes, or at least 25 minutes, or at least 30 minutes, or at least 35 minutes, or at least 40 minutes, or at least 45 minutes, or at least 50 minutes, or at least 55 minutes, or at least 60 minutes, or at least 65 minutes, or at least 70 minutes or at least 75 minutes, or at least 80 minutes, or at least 85 minutes, or at least 90 minutes, or at least 120 minutes, or at least 180 minutes. Preferably the reaction time is at least 1 minute and up to 90 minutes.

In case the method according to the invention is performed in a fed-batch manner the reaction time of the first step is the time starting from the point in time when feeding of the last educt, e.g. the ammonia and/or at least one primary/secondary amine or glycolaldehyde is stopped and the point in time that the first step is terminated. Termination of the first step can occur by cooling the reaction mixture, evacuating the reactor mixture from the vessel, e.g. to intermediate storage, intermediate purification or transfer to second vessel to perform the second step, or when the second step is initiated in the first vessel, e.g. by supplying hydrogen to the vessel. The reaction time of the second step is the time range starting from the point in time when the feeding of hydrogen is stopped and the point in time when a constant value of the pressure during the reaction is observed, i.e. the reaction is completed.

In particular, the reaction time can be at least 1 second, or at least 30 seconds, or at least 1 minute, or at least 5 minutes, or at least 10 minutes, or at least 15 minutes, or at least 20 minutes, or at least 25 minutes, or at least 30 minutes, or at least 35 minutes, or at least 40 minutes, or at least 45 minutes, or at least 50 minutes, or at least 55 minutes, or at least 60 minutes, or at least 65 minutes, or at least 70 minutes or at least 75 minutes, or at least 80 minutes, or at least 85 minutes, or at least 90 minutes, or at least 120 minutes, or at least 180 minutes and up to 5 hours. Preferably the reaction time is at least 1 minute and up to 90 minutes.

The process according to the invention can be performed batchwise, fed-batch or semi continuously. Typical reactors are high-pressure stirred tank reactors, autoclaves, fixed bed reactors, fluidized bed reactors, moving beds, circulating beds, etc. the reactor used in each case being that suitable for the desired reaction conditions (such as temperature, pressure and residence time).

The pressurization of the reaction vessel can be achieved by e.g. loading the closed reaction vessel with hydrogen and/or nitrogen until the desired reaction pressure is achieved. Only after the reaction is completed, the product (mixture) is discharged from the reaction vessel and the reaction vessel can be either cleaned if necessary, or filled again with educts. In case of the method according to the invention the first step and the second step can also performed in the same reaction vessel or in two different reaction vessels. The (intermediate) product mixture obtained in the first step can be either transferred into a second reaction vessel in order to undergo the second step there or it can remain in the same reaction vessel and the reaction conditions (e.g. supply of hydrogen) are changed to those of the second step.

Further, in case of the method according to the invention, it is also possible to include a cooling step and/or a compound removing step, like a degassing step, between the end of the first step and the beginning of the second step, independently from performing the first and the second step in one reaction vessel or two different reaction vessels Suitable reaction vessels for performing the methods according to the invention in a batchwise manner are for example stirred tank reactors, autoclaves, loop reactors or gas lift reactors.

The reaction pressure is preferably kept constant e.g. by means of a pressure regulator, if the methods according to the invention is performed in fed-batch manner. Suitable reaction vessels for performing the methods according to the invention in a fed-batch manner are for example stirred tank reactors, stirred autoclaves, loop reactors or gas lift reactors.

In case of the method according to the invention, the first step can be performed in in batch mode and the second step can be performed in fed batch mode by e.g. supplying hydrogen to the reaction mixture. It is also possible that in case of the method according to the invention the first step is performed in fed batch mode and the second step in batch mode After the reaction of glycolaldehyde, hydrogen and the ammonia and/or at least one primary amine and/or at least one secondary amine is completed, a reaction effluent is obtained. The reaction effluent contains at least one (N-substituted) alkanolamine and/or at least one (N-substituted) diamine as desired product (mixture). The reaction effluent can further contain additional organic solvent, residues of educts, co-products (e.g. co-produced water), by-products, supported hydrogenation catalyst or mixtures thereof.

Depending on the composition of the reaction effluent, the reaction effluent can be either purified or can be processed further directly without any purification.

In case solid impurities, e.g. supported hydrogenation catalyst are present in the reaction effluent, then these impurities can be removed e.g. by filtration, centrifugation or settlement and thus the reaction effluent is purified. Such a solid separation system can also be built into the reactor, prohibiting supported hydrogenation catalyst particles to leave the reactor with the effluent stream.

In case liquid, respectively dissolved impurities are present in the reaction effluent, e.g. by-products, then these impurities can be removed e.g. by distillation, decantation, pervaporation, ultrafiltration or other suitable separation methods in order to purify the reaction effluent.

In general, the purification of the reaction effluent is not a mandatorily necessary measure. The reaction effluent can be analyzed e.g. by gas-chromatographic analysis and depending on the outcome of the analysis it can be decided if further purification is necessary.

The reaction products obtained by the methods according to the invention can be used as building block for surfactants and fabric softener, as epoxy curing agent, as catalyst for manufacturing polyurethane, or as ligand for metals without any further purification.

EXAMPLES

The examples are to be understood as illustrating the method according to the invention. The examples are however not to be construed as limiting the scope of the invention.

Example 1-6

An electrically heated 50 ml autoclave (Hastelloy) with a mechanical magnet-coupled stirrer was charged with 0.5 g of commercial dimeric glycolaldehyde in the particular organic solvent (15 ml) and 200 µl triethylene glycol dimethyl ether as internal standard. Subsequently, the amount of the catalyst specified in Table 1 was added. Next, dimethylamine, according to the molar ratio specified in Table 1 (dimethylamine:monomeric glycolaldehyde), was metered in and the mixture was pressurized to 70 bar of hydrogen and heated to 100° C. Stirring was effected at 100° C. and the particular pressure for 1 h. The reaction output was filtered off from the catalyst after 1 h and analyzed by GC (carbon percent, meaning the amount of substrate carbon atoms that can be detected as end products, with the internal standard as a reference) The conversion is 100% and the difference from 100% mass balance is unidentified secondary components.

Comparative Example 1-4

An electrically heated 50 ml autoclave (Hastelloy) with a mechanical magnet-coupled stirrer was charged with 0.5 g of commercial dimeric glycolaldehyde in the particular solvent (15 ml) and 200 µl triethylene glycol dimethyl ether as internal standard. Subsequently, the amount of the catalyst specified in Table 1 was added. Next, dimethylamine, according to the molar ratio specified in Table 1 (dimethylamine:monomeric glycolaldehyde), was metered in and the mixture was pressurized to 70 bar of hydrogen and heated to 100° C. Stirring was effected at 100° C. and the particular pressure for 1 h. The reaction output was filtered off from the catalyst after 1 h and analyzed by GC (carbon percent, meaning the amount of substrate carbon atoms that can be detected as end products, with the internal standard as a reference) The conversion is 100% and the difference from 100% mass balance is unidentified secondary components.

TABLE 1

Amination of glycolaldehyde with Dimethylamine

| Example | Catalyst | Amount of cat. (g) | Solvent | Molar ratio of DMA:GA | DMAE (C %) | TMEDA (C %) | EG (C %) |
|---|---|---|---|---|---|---|---|
| 1 | Ru/C (5 wt. %) | 0.13 | IPA | 1:1 | 59.8 | 2.3 | 0.0 |
| 2 | Ru/C (5 wt. %) | 0.13 | EtOH | 1:1 | 77.7 | 7.8 | 13.3 |
| 3 | Ru/C (5 wt. %) | 0.13 | MeOH | 1:1 | 87.65 | 7.1 | 4.6 |
| 4 | Pd/C (5 wt. %) | 0.13 | IPA | 1:1 | 62.0 | 0.7 | 0.0 |
| 5 | Pd/C (5 wt. %) | 0.13 | EtOH | 1:1 | 93.0 | 1.3 | 4.2 |
| 6 | Pd/C (5 wt. %) | 0.13 | MeOH | 1:1 | 97.2 | 1.8 | 1.0 |
| Comp. 1 | Ru/C (5 wt. %) | 0.13 | $H_2O$ | 1:1 | 34.7 | 4.8 | 11.0 |
| Comp. 2 | Pd/C (5 wt. %) | 0.13 | $H_2O$ | 1:1 | 67.3 | 2.4 | 0.4 |
| Comp. 3 | Ru/C (5 wt. %) | 0.13 | THF | 1:1 | 41.4 | 0.3 | 0.0 |
| Comp. 4 | Pd/C (5 wt. %) | 0.13 | THF | 1:1 | 56.9 | 0.4 | 0.0 |

Examples 1 to 6 in comparison with Comparative Examples 3 to 4 demonstrate the advantage of using a reactive organic fluid or solvent in comparison with aprotic solvents such as THF. Examples 1 to 6 in comparison with Comparative Examples 1 to 2 demonstrate that the obtained increase in yield is not merely an effect of removing water from the reaction mixture, since the obtained yields are different for each reactive organic fluid or solvent.

Example 7-11

An electrically heated 50 ml autoclave (Hastelloy) with a mechanical magnet-coupled stirrer was charged with 1 g of commercial dimeric glycolaldehyde in the particular organic solvent (25 ml) and 400 µl triethylene glycol dimethyl ether as internal standard. Subsequently, the amount of the catalyst specified in Table 2 was added. Next, ammonia, according to the molar ratio specified in Table 2 (ammonia:monomeric glycolaldehyde), was metered in and the mixture was pressurized to 70 bar of hydrogen and heated to 100° C. Stirring was effected at 100° C. and the particular pressure for 1 h. The reaction output was filtered off from the catalyst after 1 h and analyzed by GC (carbon percent, meaning the amount of substrate carbon atoms that can be detected as end products, with the internal standard as a reference) The conversion is 100% and the difference from 100% mass balance is unidentified secondary components.

Comparative Example 5

An electrically heated 50 ml autoclave (Hastelloy) with a mechanical magnet-coupled stirrer was charged with 1 g of commercial dimeric glycolaldehyde in the particular organic solvent (10 ml) and 150 µl diethylene glycol dimethyl ether as internal standard. Subsequently, the amount of the catalyst specified in Table 2 was added, suspended in 5 ml of THF. Next, ammonia, according to the molar ratio specified in Table 2 (ammonia:monomeric glycolaldehyde), was metered in and the mixture was pressurized to 40 bar of hydrogen and heated to 100° C. On attainment of the reaction temperature, additional hydrogen was injected that the reaction pressure reached 100 bar. Stirring was effected at 100° C. and the particular pressure for 8 h. The reaction output was filtered off from the catalyst after 8 h and analyzed by GC (carbon percent, meaning the amount of substrate carbon atoms that can be detected as end products, with the internal standard as a reference) The conversion is 100% and the difference from 100% mass balance is unidentified secondary components.

TABLE 2

Amination of glycolaldehyde with ammonia

| Example | Catalyst | Amount of cat. (g) | Solvent | Molar ratio of NH3:GA | MEOA (C %) | EDA (C %) | DEOA (C %) | TEOA (C %) | EG (C %) |
|---|---|---|---|---|---|---|---|---|---|
| 7 | Pd/C (5 wt. %) | 0.25 | MeOH | 12:1 | 26.8 | 0.0 | 56.0 | 4.7 | 0.0 |
| 8 | Pd/C (5 wt. %) | 0.25 | MeOH | 6:1 | 10.0 | 0.0 | 70.1 | 12.9 | 4.5 |
| 9 | Pd/C (5 wt. %) | 0.25 | MeOH | 3:1 | 7.7 | 0.0 | 59.5 | 27.0 | 5.0 |

TABLE 2-continued

Amination of glycolaldehyde with ammonia

| Example | Catalyst | Amount of cat. (g) | Solvent | Molar ratio of NH3:GA | MEOA (C %) | EDA (C %) | DEOA (C %) | TEOA (C %) | EG (C %) |
|---|---|---|---|---|---|---|---|---|---|
| 10 | Pd/C (5 wt. %) | 0.25 | MeOH | 1:2 | 0.0 | 0.0 | 29.0 | 65.0 | 5.9 |
| 11 | Pd/C (5 wt. %) | 0.25 | MeOH | 1:3 | 0.0 | 0.0 | 6.6 | 77.2 | 12.5 |
| Comp. 5 | Ni-6458P | 0.5 | H$_2$O | 35:1 | 45.0 | 0.0 | 0.0 | 0.0 | 0.0 |
| Comp. 6 | Ni-6458P | 0.5 | H$_2$O | 4:1 | 15.0 | 0.0 | 0.0 | 0.0 | 0.0 |

Example 7 in comparison with Comparative Example 5 demonstrates that a better mass balance with higher yields can readily be obtained at lower molar amine ratio with the method according to the invention, in comparison with the current method found in prior art. Higher yields and better control over selectivity can obtained when this method according to the invention is conducted in presence of a reactive organic fluid or solvent, than compared with H$_2$O. Moreover, Examples 5-9 in comparison with Comparative examples 5-6 demonstrate that the selectivity towards end-products can be successfully altered by applying an adequate molar ratio of NH3:GA in the one-pot method according to the invention, in comparison with the current method found in prior art.

Example 12-15

An electrically heated 50 ml autoclave (Hastelloy) with a mechanical magnet-coupled stirrer was charged with 1 g of commercial dimeric glycolaldehyde in the particular organic solvent (25 ml) and 200 μl triethylene glycol dimethyl ether as internal standard. Subsequently, the amount of the catalyst specified in Table 3 was added. Next, monomethylamine, according to the molar ratio specified in Table 3 (monomethylamine:monomeric glycolaldehyde), was metered in and the mixture was pressurized to 70 bar of hydrogen and heated to 100° C. Stirring was effected at 100° C. and the particular pressure for 1 h. The reaction output was filtered off from the catalyst after 1 h and analyzed by GC (carbon percent, meaning the amount of substrate carbon atoms that can be detected as end products, with the internal standard as a reference) The conversion is 100% and the difference from 100% mass balance is unidentified secondary components.

Comparative Example 7-15

An electrically heated 50 ml autoclave (Hastelloy) with a mechanical magnet-coupled stirrer was charged with 1 g of commercial dimeric glycolaldehyde in the particular organic solvent (25 ml) and 400 μl triethylene glycol dimethyl ether as internal standard. Subsequently, the amount of the catalyst specified in Table 3 was added. Next, monomethylamine, according to the molar ratio specified in Table 3 (N-monomethylamine1:monomeric glycolaldehyde), was metered in and the mixture was pressurized to 70 bar of hydrogen and heated to 100° C. Stirring was effected at 100° C. and the particular pressure for 1 h. The reaction output was filtered off from the catalyst after 1 h and analyzed by GC (carbon percent, meaning the amount of substrate carbon atoms that can be detected as end products, with the internal standard as a reference) The conversion is 100% and the difference from 100% mass balance is unidentified secondary components.

Comparative Example 16

An electrically heated 50 ml autoclave (Hastelloy) with a mechanical magnet-coupled stirrer was charged with 0.5 g of commercial dimeric glycolaldehyde in the particular organic solvent (25 ml) and 200 μl triethylene glycol dimethyl ether as internal standard. Subsequently, the amount of the catalyst specified in Table 4 was added. Next, N-methylaminoethanol, according to the molar ratio specified in Table 4 (N-methylaminoethanol:monomeric glycolaldehyde), was metered in and the mixture was pressurized to 70 bar of hydrogen and heated to 100° C. Stirring was effected at 100° C. and the particular pressure for 1 h. The reaction output was filtered off from the catalyst after 1 h and analyzed by GC (carbon percent, meaning the amount of substrate carbon atoms that can be detected as end products, with the internal standard as a reference) The conversion is 100% and the difference from 100% mass balance is unidentified secondary components.

TABLE 3

Amination of glycolaldehyde with Monomethylamine

| Example | Catalyst | Amount of cat. (g) | Solvent | Molar ratio of MMA:GA | MAE (C %) | MDEA (C %) | DMEDA (C %) | EG (C %) |
|---|---|---|---|---|---|---|---|---|
| 12 | Pd/C (5 wt. %) | 0.25 | MeOH | 6:1 | 91.8 | 0.0 | 4.5 | 0.0 |
| 13 | Pd/C (5 wt. %) | 0.25 | MeOH | 3:1 | 90.0 | 3.0 | 5.4 | 0.0 |
| 14 | Pd/C (5 wt. %) | 0.25 | MeOH | 1:1 | 64.1 | 18.2 | 0.0 | 0.0 |
| 15 | Pd/C (5 wt. %) | 0.25 | MeOH | 1:2 | 0.0 | 90.7 | 0.0 | 8.0 |

TABLE 3-continued

Amination of glycolaldehyde with Monomethylamine

| Example | Catalyst | Amount of cat. (g) | Solvent | Molar ratio of MMA:GA | MAE (C %) | MDEA (C %) | DMEDA (C %) | EG (C %) |
|---|---|---|---|---|---|---|---|---|
| Comp. 7 | Ni-6458P | 0.25 | H₂0 | 8:1 | 85.0 | 0.0 | 15.0 | 0.0 |
| Comp. 8 | Ni-6458P | 0.25 | H₂0 | 4:1 | 65.0 | 0.0 | 15.0 | 0.0 |
| Comp. 9 | Ni-6458P | 0.25 | H₂0 | 2:1 | 22.0 | 0.0 | 8.0 | 0.0 |
| Comp. 10 | Ni-6458P | 0.25 | H₂0 | 1:1 | 17.0 | 0.0 | 3.0 | 0.0 |
| Comp. 11 | Pd/C (5 wt. %) | 0.25 | H₂0 | 1:1 | 40.0 | 28.0 | 1.0 | 0.0 |
| Comp. 12 | Pd/C (5 wt. %) | 0.25 | H₂0 | 8:1 | 91.1 | 0.0 | 5.1 | 3.8 |
| Comp. 13 | Pd/C (5 wt. %) | 0.25 | H₂0 | 1:2 | 14.1 | 65.4 | 0.0 | 3.8 |
| Comp. 14 | Pd/C (5 wt. %) | 0.25 | THF | 1:1 | 46.0 | 37.1 | 1.1 | 0.2 |
| Comp. 15 | Pd/C (5 wt. %) | 0.25 | THF | 1:2 | 0.0 | 69.5 | 0.0 | 13.1 |

TABLE 4

Amination of glycolaldehyde with N-methylaminoethanol

| Example | Catalyst | Amount of cat. (g) | Solvent | Molar ratio of MAE:GA | MAE (C %) | MDEA (C %) | DMEDA (C %) | EG (C %) |
|---|---|---|---|---|---|---|---|---|
| Comp. 16 | Pd/C (5 wt. %) | 0.25 | MeOH | 7:1 | 99 | 0.0 | 0.0 | 0.0 |

Examples 12-15 in comparison with Comparative examples 7-15 demonstrate that the selectivity towards end-products can be successfully altered by applying an adequate molar ratio of MMA:GA in the method according to the invention. Higher yields and better control over selectivity can obtained when this method according to the invention is conducted in presence of a reactive organic fluid or solvent, than compared with H2O or aprotic solvents such as THF. Example 15 in comparison with Comparative example 16 demonstrates that similar yields of the higher alkanolamines can already be obtained in a one-pot process according to the invention, compared with a two-pot process found in the prior art wherein the applied amine is already derived from glycolaldehyde. Moreover, when both N-methylaminethanol and N-methyldiethanolamine are obtained in a two-pot process with 90% and 99% yield respectively, as demonstrated in Example 12 and Comparative example 16, the overall mass balance of glycolaldehyde is only 89%, which is lower than the one-pot process demonstrated in Example 13.

Example 16-18

An electrically heated 50 ml autoclave (Hastelloy) with a mechanical magnet-coupled stirrer was charged with 0.5 g of commercial dimeric glycolaldehyde in the particular organic solvent (25 ml) and 200 μl triethylene glycol dimethyl ether as internal standard. Subsequently, the amount of the catalyst specified in Table 5 was added. Next, dimethylamine, according to the molar ratio specified in Table 5 (dimethylamine:monomeric glycolaldehyde), was metered in and the mixture was pressurized to 35 bar of nitrogen at room temperature. Stirring was effected at the particular pressure for 1 h. Next, the inert atmosphere was vented and the mixture was pressured to 70 bar of hydrogen at the reaction temperature and for the reaction time specified in Table 5. The reaction output was filtered off from the catalyst and analyzed by GC (carbon percent, meaning the amount of substrate carbon atoms that can be detected as end products, with the internal standard as a reference) The conversion is 100% and the difference from 100% mass balance is unidentified secondary components.

Example 19

An electrically heated 50 ml autoclave (Hastelloy) with a mechanical magnet-coupled stirrer was charged with 1 g of commercial dimeric glycolaldehyde in the particular organic solvent (25 ml) and 200 μl triethylene glycol dimethyl ether as internal standard. Subsequently, the amount of the catalyst specified in Table 6 was added. Next, monomethylamine, according to the molar ratio specified in Table 6 (dimethylamine:monomeric glycolaldehyde), was metered in and the mixture was pressurized to 35 bar of nitrogen at room temperature. Stirring was effected at the particular pressure for 1 h. Next, the inert atmosphere was vented and the mixture was pressured to 70 bar of hydrogen at the reaction temperature and for the reaction time specified in Table 6. The reaction output was filtered off from the catalyst and analyzed by GC (carbon percent, meaning the amount of substrate carbon atoms that can be detected as end products, with the internal standard as a reference) The conversion is 100% and the difference from 100% mass balance is unidentified secondary components.

Comparative Example 17-18

An electrically heated 50 ml autoclave (Hastelloy) with a mechanical magnet-coupled stirrer was charged with 0.5 g of commercial dimeric glycolaldehyde in the particular organic solvent (25 ml) and 200 µl triethylene glycol dimethyl ether as internal standard. Subsequently, the amount of the catalyst specified in Table 5 was added. Next, dimethylamine, according to the molar ratio specified in Table 5 (dimethylamine:monomeric glycolaldehyde), was metered in and the mixture was pressurized to 35 bar of nitrogen at room temperature. Stirring was effected at the particular pressure for 1 h. Next, the inert atmosphere was vented and the mixture was pressured to 70 bar of hydrogen at the reaction temperature and for the reaction time specified in Table 5. The reaction output was filtered off from the catalyst and analyzed by GC (carbon percent, meaning the amount of substrate carbon atoms that can be detected as end products, with the internal standard as a reference) The conversion is 100% and the difference from 100% mass balance is unidentified secondary components.

Examples 16-18 compared to Comparative example 17 and Example 19 compared to Example 15 demonstrates that the selectivity towards end-products can be successfully altered and enhanced by applying a two-step one-pot method according to the invention, compared with a traditional one-step procedure. Depending on the molar amine to substrate ratio, the selectivity will be shifted either towards diamines (Examples 16-18) or higher alkanolamines (Example 19). Examples 16-18 compared to Comparative example 18 further demonstrates that this two-step procedure is most pronounced in the presence of a reactive fluid or solvent according to the present invention, in comparison with aprotic solvents such as THF, that does not comprises labile proton like a hydroxyl proton or carboxylic acid proton or that does not has a hydrogen atom bonded to an electronegative atom, yielding highly polarized bonds in which the hydrogen has protonlike character and can have hydrogen bonding characteristics Example 20-25

A series of 5 wt % Ni on various supports were prepared by incipient wetness impregnation. An aqueous solution of nickel nitrate was added dropwise to a support, chosen from Aerosil 380, Alumina, carbon, TiO2 or MgO. The resulting suspension was then dried at 60° C. to obtain a catalyst precursor. Activation of the catalyst was performed by reduction under a hydrogen flow, at a heating rate of 5° C./minute up to 500° C. which was hold for one hour. An electrically heated 50 ml autoclave (Hastelloy) with a mechanical magnet-coupled stirrer was charged with 0.5 g of commercial dimeric glycolaldehyde in methanol (25 ml) and 200 µl triethylene glycol dimethyl ether as internal standard. Subsequently, the amount of the catalyst specified

TABLE 5

Amination of glycolaldehyde with Dimethylamine in a two-step one-pot procedure

| Example | Catalyst | Amount of cat. (g) | Solvent | Temp. (° C.) | Time under Nitrogen at RT (h) | Molar ratio of DMA:GA | DMAE (C %) | TMEDA (C %) | EG (C %) |
|---|---|---|---|---|---|---|---|---|---|
| 16 | Pd/C (5 wt. %) | 0.5 | EG | 100 | 1 | 3:1 | 36.7 | 48.1 | 0.0 |
| 17 | Pd/C (5 wt. %) | 0.5 | EG | 100 | 5 | 12:1 | 8.8 | 59.5 | 0.0 |
| 18 | Pd/C (5 wt. %) | 0.5 | EG | 130 | 5 | 12:1 | 3.0 | 90.1 | 0.0 |
| Comp. 17 | Pd/C (5 wt. %) | 0.5 | EG | 100 | 0 | 3:1 | 72.4 | 4.8 | 0.0 |
| Comp. 18 | Pd/C (5 wt. %) | 0.5 | THF | 100 | 1 | 3:1 | 90.5 | 6.8 | 0.0 |

TABLE 6

Amination of glycolaldehyde with Monomethylamine in a two-step one-pot procedure

| Example | Catalyst | Amount of cat. (g) | Solvent | Temp. (° C.) | Time under Nitrogen at RT (h) | Molar ratio of DMA:GA | MAE (C %) | MDEA (C %) | DMEDA (C %) | EG (C %) |
|---|---|---|---|---|---|---|---|---|---|---|
| 15 | Pd/C (5 wt. %) | 0.25 | MeOH | 100 | 0 | 1:2 | 0.0 | 90.7 | 0.0 | 8.0 |
| 19 | Pd/C (5 wt. %) | 0.4 | MeOH | 100 | 1 | 1:2 | 0.0 | 93 | 0.0 | 7.0 | in Table 7 was added. Next, dimethylamine, according to the molar ratio specified in Table 7 (dimethylamine:monomeric glycolaldehyde), was metered in and the mixture was pressurized to 70 bar of hydrogen at the reaction temperature of 100° C. during one hour. The reaction output was filtered off from the catalyst and analyzed by GC (carbon percent, meaning the amount of substrate carbon atoms that can be detected as end products, with the internal standard as a reference) The conversion is 100% and the difference from 100% mass balance is unidentified secondary components.

TABLE 7

| Example | Catalyst | Molar ratio of DMA:GA | Amount of cat. (g) | DMAE (C %) | TMEDA (C %) | EG (C %) |
|---|---|---|---|---|---|---|
| 20 | Ni/Aerosil 380 (5 wt. %) | 3:1 | 0.13 | 32.8 | 55.5 | 7.2 |
| 21 | Ni/alumina (5 wt. %) | 3:1 | 0.13 | 26.1 | 55.1 | 6.4 |
| 22 | Ni/C (5 wt. %) | 3:1 | 0.13 | 21.1 | 73.6 | 4.5 |
| 23 | Ni/TiO2 (5 wt. %) | 3:1 | 0.13 | 19.9 | 40.5 | 8.9 |
| 24 | Ni/MgO (5 wt. %) | 3:1 | 0.13 | 31.9 | 20.9 | 20.9 |

Examples 20-22 compared to examples 23-24 demonstrate that relative inert supports such as silica, alumina, or carbon are preferred to obtain a high overall mass balance (85-95 C %) compared to supports that contain an intrinsic acidity (TiO2) or basicity (MgO) function (mass balance <65%).

The invention claimed is:

1. A process for preparing alkanolamines and diamines, characterized by a two-step procedure wherein step 1 comprises under inert atmosphere and in a reactive organic fluid reacting of glycolaldehyde with an aminating agent, to give unsaturated intermediates and step 2 comprises hydrogenating the reaction mixture obtained in the first step under a hydrogen atmosphere whilst in contact with a supported hydrogenation catalyst and still in the reactive organic fluid,
   wherein the aminating agent is ammonia, a primary amine, a secondary amine, or mixtures thereof,
   wherein the reactive organic fluid comprises a polar protic organic fluid which comprises O—H or N—H bonds, and wherein the polar protic organic solvent has a dielectric constant value of between 15 to 50, and
   whereby the supported hydrogenation catalyst is, silica, silica-alumina, alumina or carbon, as support.

2. The process according to claim 1, whereby the reactive organic fluid comprises molecules that have an hydrogen atom bound to an oxygen of an hydroxyl group or bound to an nitrogen of an amine group so that the reactive organic fluid participates in the formation of unsaturated intermediates by donating protons (H+).

3. The process according to claim 1, wherein the reaction is conducted in a two-step one-pot procedure.

4. The process according to claim 1, whereby the first step comprises reacting the glycolaldehyde with an aminating agent of the groups consisting of ammonia ($NH_3$), at least one primary amine ($NH_2R$) and at least one secondary amine (NHR'R") and in contact with the reactive organic fluid to give unsaturated intermediates.

5. The process according to claim 4, whereby the aminating agent is ammonia, monomethylamine or dimethylamine.

6. The process according to claim 1, whereby the supported hydrogenation catalyst comprises Pd or Ru, as catalytically active components.

7. The process according to claim, whereby the solid catalyst supported hydrogenation catalyst is Ru/C or comprises Ru/C or is Pd/C or comprising Pd/C.

8. The process according to claim, whereby the reactions are performed at a reaction temperature of 15 to 250° C. and at a reaction pressure or a pressure during the reaction of 10 to 150 bar.

9. The process according to claim 1, whereby the alkanolamines and diamines obtained in a one-pot process starting from ammonia ($NH_3$) are monoethanolamine, diethanolamine, triethanolamine or ethylene diamine.

10. The process according to claim 1, whereby the alkanolamines and diamines obtained in a one-pot process starting from monomethylamine (MMA) are N-methylaminoethanol, N-methyldiethanolamine or N,N'-dimethylethylenediamine.

11. The process according to claim 1, whereby the alkanolamines and diamines obtained in a one-pot process starting from dimethylamine (DMA) are N,N-dimethylaminoethanol or N,N,N',N'-tetramethylethylenediamine.

12. The process according to claim 1, whereby the alkanolamines are obtained in a one-pot process with methanol as reactive organic fluid.

13. The process according to claim 1, whereby the alkanolamines are obtained in a one-pot process with methanol as reactive organic fluid and stoichiometric amine-to-substrate molar ratio according to the obtained final alkanolamine product.

14. The process according to claim 1, whereby the alkanolamines are obtained in a two-step one-pot process with methanol as reactive organic fluid.

15. The process according to claim 1, whereby the diamines are obtained in a two-step one-pot process with ethylene glycol as reactive organic fluid.

16. The process according to claim 1, whereby the reactive organic fluid is composed of or comprises molecules with 1 to 4 C atoms.

17. The process according to claim 1, whereby the reactive organic fluid is an alcohol of the group consisting of methanol, ethanol and ethylene glycol.

* * * * *